United States Patent
Scribner et al.

(10) Patent No.: US 7,252,671 B2
(45) Date of Patent: Aug. 7, 2007

(54) SYSTEMS AND METHODS FOR TREATING VERTEBRAL BODIES

(75) Inventors: Robert M Scribner, Niwot, CO (US); Michael L. Reo, Redwood City, CA (US); Mark A Reiley, Piedmont, CA (US); Ryan P Boucher, San Francisco, CA (US); Paul M Sand, San Carlos, CA (US)

(73) Assignee: Kyphon Inc., Sunnyvale, CA (US)

( * ) Notice: Subject to any disclaimer, the term of this patent is extended or adjusted under 35 U.S.C. 154(b) by 478 days.

(21) Appl. No.: 10/640,790

(22) Filed: Aug. 14, 2003

(65) Prior Publication Data

US 2004/0049203 A1    Mar. 11, 2004

Related U.S. Application Data

(60) Division of application No. 09/905,170, filed on Jul. 13, 2001, now Pat. No. 6,641,587, which is a continuation-in-part of application No. 09/597,646, filed on Jun. 20, 2000, now Pat. No. 6,716,216, which is a continuation-in-part of application No. 09/134,323, filed on Aug. 14, 1998, now Pat. No. 6,241,734, said application No. 09/905,170.

(60) Provisional application No. 60/218,237, filed on Jul. 14, 2000.

(51) Int. Cl.
*A61F 5/00* (2006.01)

(52) U.S. Cl. .......................... 606/86; 606/93

(58) Field of Classification Search .................. 606/93; 604/218, 222

See application file for complete search history.

(56) References Cited

U.S. PATENT DOCUMENTS

| 2,888,923 | A | * | 6/1959 | Da Cunha Reis | 604/194 |
| 3,660,037 | A | * | 5/1972 | Sokol | 422/73 |
| 3,985,122 | A | * | 10/1976 | Topham | 600/578 |
| 4,005,527 | A | | 2/1977 | Wilson et al. | |
| 4,512,351 | A | * | 4/1985 | Pohndorf | 607/117 |
| 4,919,153 | A | | 4/1990 | Chin | |

(Continued)

FOREIGN PATENT DOCUMENTS

EP    0 890 341    1/1999

(Continued)

*Primary Examiner*—Edjardo C. Robert
*Assistant Examiner*—Annette Reimers
(74) *Attorney, Agent, or Firm*—Ryan, Kromholz, and Manion S.C.

(57) ABSTRACT

A filler instrument comprises a first chamber section having a first cross sectional area and a second chamber section having a second cross sectional area less than the first cross sectional area. The second chamber section communicates with the first chamber section. The first chamber section includes an inlet for receiving a material into the filler instrument, and the second chamber section includes an outlet for discharging the material from the filler instrument. A first plunger is sized to pass through the first chamber section and not the second chamber section. A second plunger is sized to pass through an interior bore of the first plunger and into the second chamber section. In use, the first plunger displaces material residing in the first chamber section through the second chamber section toward the outlet, and the second plunger displaces material residing in the second chamber section through the outlet.

8 Claims, 20 Drawing Sheets

U.S. PATENT DOCUMENTS

| | | | |
|---|---|---|---|
| 4,969,888 A * | 11/1990 | Scholten et al. | 606/94 |
| 5,013,318 A | 5/1991 | Spranza, III | |
| 5,171,248 A | 12/1992 | Ellis | |
| 5,385,566 A | 1/1995 | Ullmark et al. | |
| 5,462,740 A * | 10/1995 | Evenstad et al. | 424/436 |
| 5,468,245 A | 11/1995 | Vargas, III | |
| 5,512,054 A | 4/1996 | Morningstar | |
| 5,514,137 A | 5/1996 | Coutts | |
| 5,658,310 A | 8/1997 | Berger | |
| 5,989,260 A | 11/1999 | Yao | |
| 5,997,581 A | 12/1999 | Khalili | |
| 6,017,348 A | 1/2000 | Hart et al. | |
| 6,146,358 A | 11/2000 | Rowe | |
| 6,241,734 B1 | 6/2001 | Scribner et al. | |
| 6,641,587 B2 * | 11/2003 | Scribner et al. | 606/93 |

FOREIGN PATENT DOCUMENTS

| | | |
|---|---|---|
| WO | 98/56301 | 1/1998 |
| WO | 99/51149 | 1/1999 |
| WO | WO 99/49819 | 10/1999 |
| WO | WO 99/62416 | 12/1999 |
| WO | WO 00/67650 | 11/2000 |

* cited by examiner

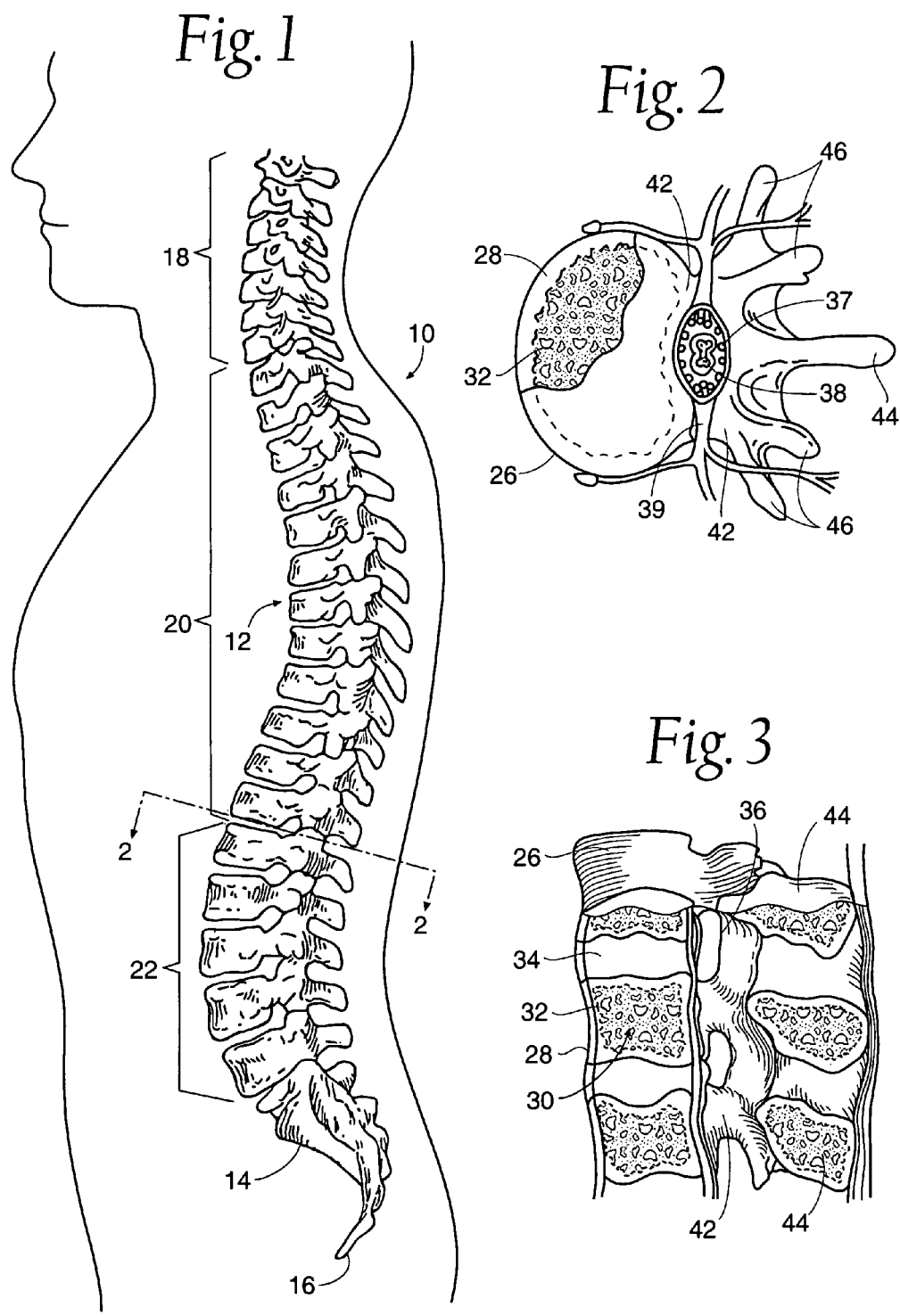

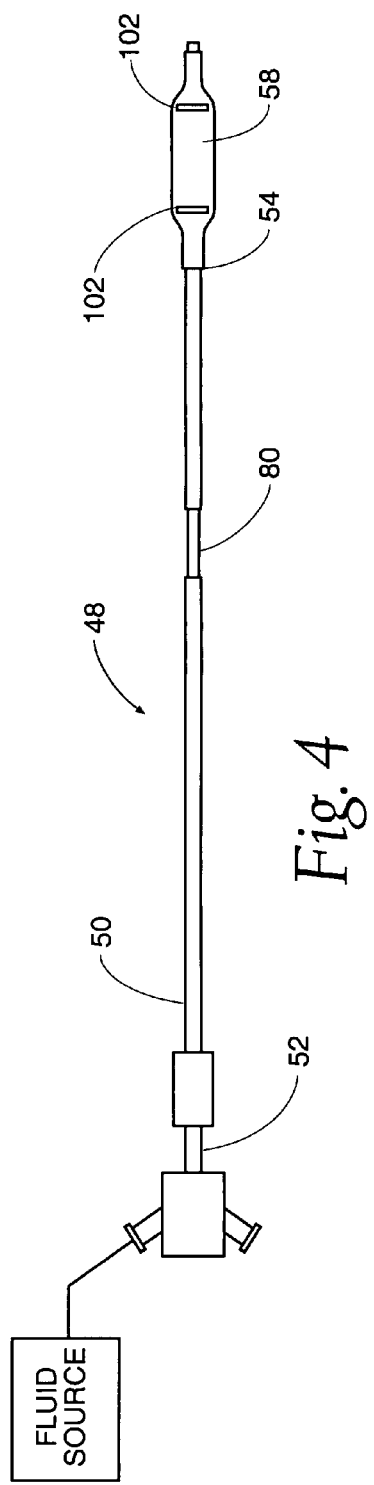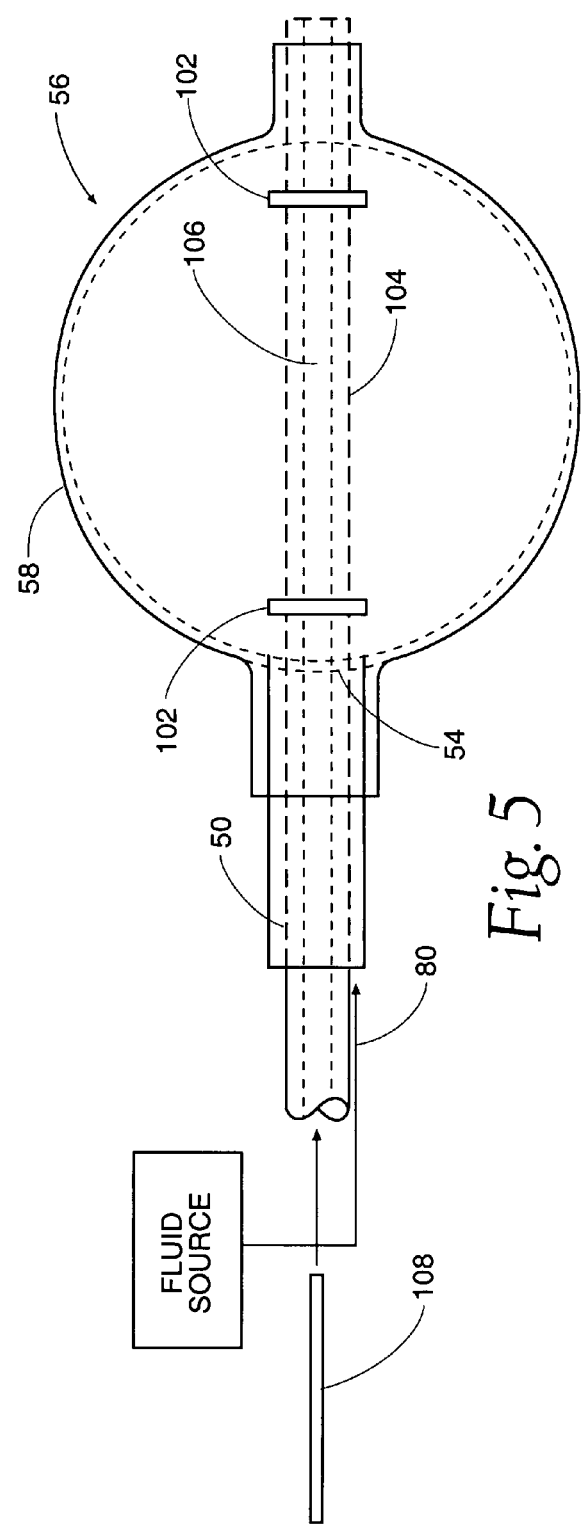

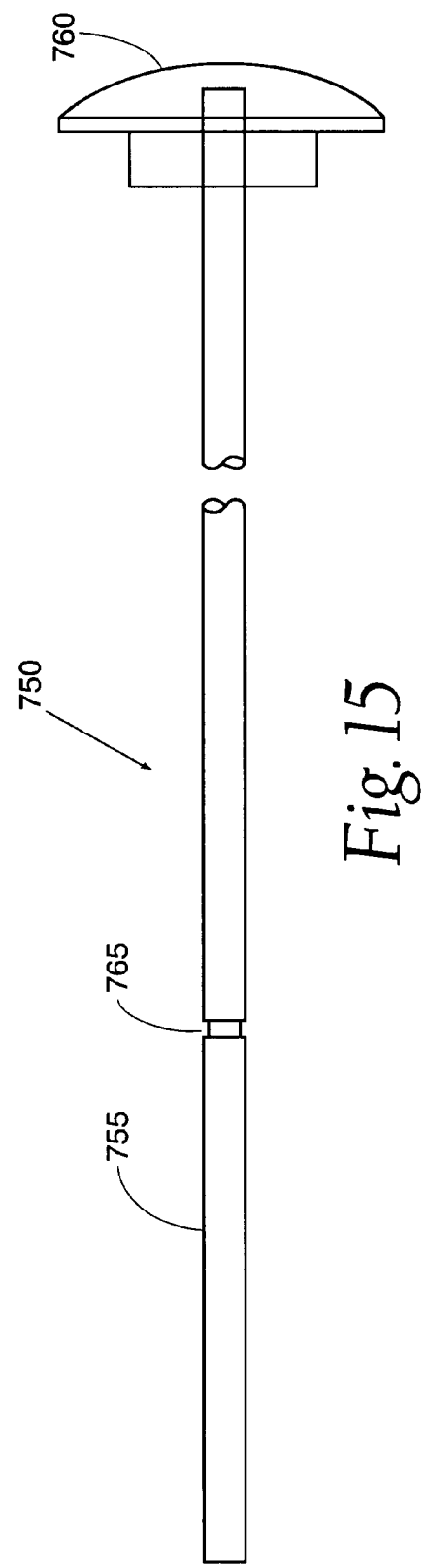

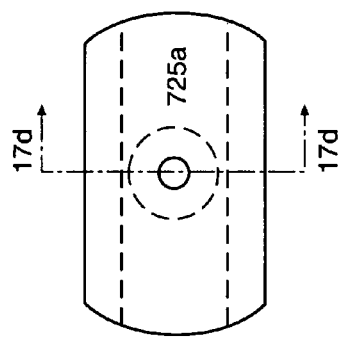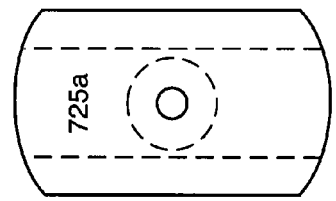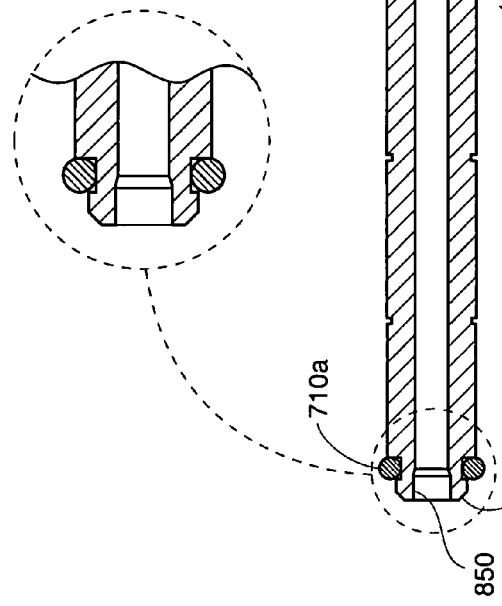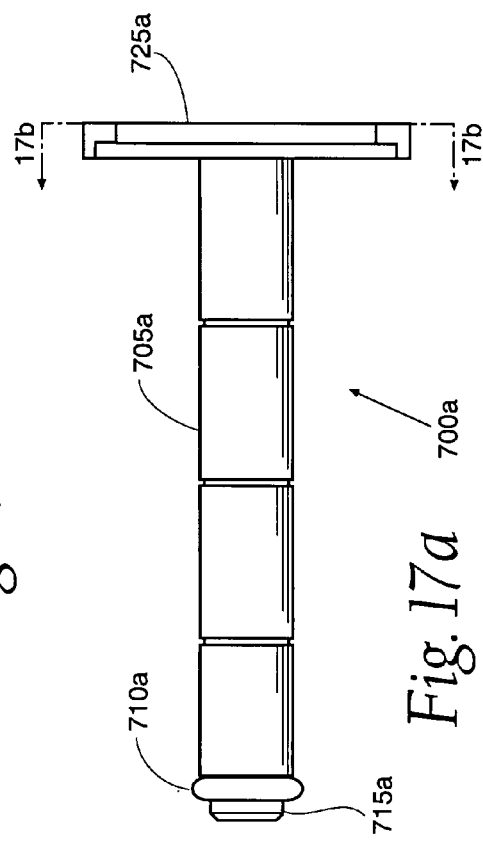

SYSTEMS AND METHODS FOR TREATING VERTEBRAL BODIES

RELATED APPLICATIONS

This application is a divisional of Ser. No. 09/905,170 filed Jul. 13, 2001, now U.S. Pat. No. 6,641,587, which is a continuation-in-part of Ser. No. 09/597,646 filed Jun. 20, 2000 now U.S. Pat. No. 6,716,216, which is a continuation-in-part of Ser. No. 09/134,323 filed Aug. 14, 1998, and entitled Systems and Methods for Placing Materials into Bone, now U.S. Pat. No. 6,241,734, and which claims the benefit of provisional application Ser. No. 60/218,237 filed Jul. 14, 2000.

FIELD OF THE INVENTION

The invention generally relates to the treatment of bone conditions in humans and other animals.

BACKGROUND OF THE INVENTION

The deployment of expandable structures, generically called "balloons," into cancellous bone is known. For example, U.S. Pat. Nos. 4,969,888 and 5,108,404 disclose apparatus and methods using expandable structures in cancellous bone for the fixation of fractures or other osteoporotic and non-osteoporotic conditions of human and animal bones.

As part of a fracture fixation procedure, bone cement or other therapeutic compound, can be injected into a targeted bone to repair and/or augment the target bone. Several companies offer bone cement injection devices. These devices are similar to a household caulking gun. Typically, the injection device has a pistol-shaped body, which supports a cartridge containing bone cement. The cement is typically in two-parts and must be mixed in a mixer and transferred into the cartridge for injection.

Just after mixing, and prior to curing, the cement is in a flowing, viscous liquid state, similar to a syrup or watery pancake batter in consistency. The injection device has a ram, which is actuated by a manually movable trigger or screwing mechanism for pushing the viscous bone cement out the front of the cartridge through a suitable nozzle and into the interior of a bone targeted for treatment.

Once injected into the targeted bone, the cement undergoes a curing cycle of perhaps 6 to 8 minutes. While curing, the cement passes from a viscous liquid to a putty-like consistency and finally to a hard rigid block.

SUMMARY OF THE INVENTION

The invention provides, in its various aspects, greater control over the placement of cement and other flowable liquids into bone. Moreover, the invention facilitates the injection of highly viscous filling material into the bone, either into a cavity formed within the bone, or directly into the bone.

Features and advantages of the inventions are set forth in the following Description and Drawings, as well as in the appended Claims.

BRIEF DESCRIPTION OF THE DRAWINGS

FIG. 1 is a lateral view of a human spinal column;

FIG. 2 is a representative coronal view, with portions broken away and in section, of a human vertebral body, which is part of the spinal column shown in FIG. 1;

FIG. 3 is a lateral view, with portions broken away and in section, of several vertebral bodies, which are part of the spinal column shown in FIG. 1;

FIG. 4 is a plan view of a tool which carries at its distal end an expandable structure, which, in use, compresses cancellous bone, the structure being shown in a collapsed condition;

FIG. 5 is enlarged side view of the expandable structure carried by the tool shown in FIG. 4;

FIG. 15 is a side view of one embodiment of a second ram assembly constructed in accordance with the teachings of the present invention;

FIGS. 17A through 17D are views of an alternate embodiment of a first ram assembly constructed in accordance with the teachings of the present invention;

Figure 6:
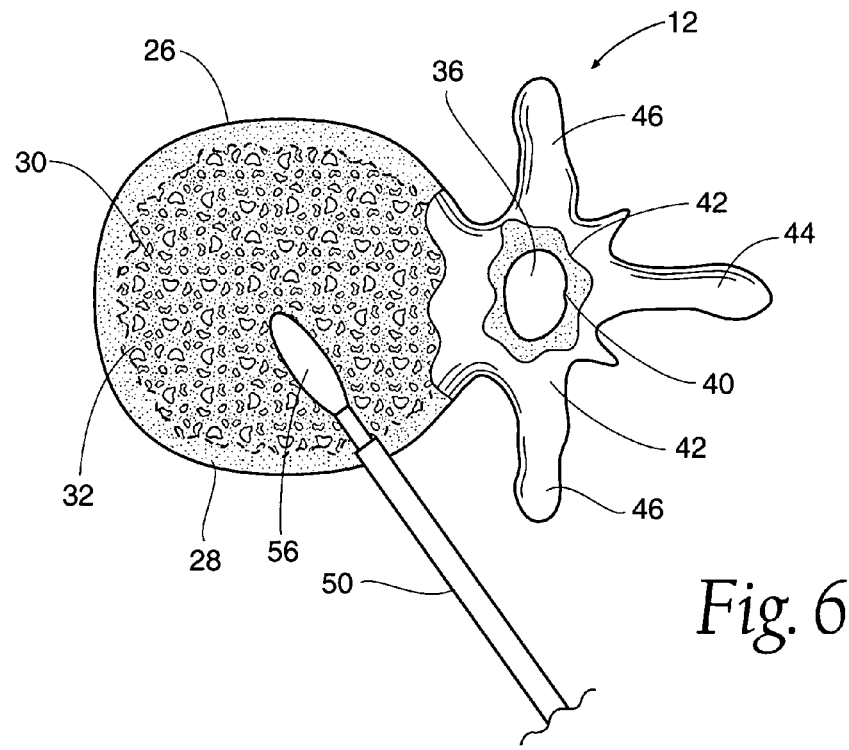
FIG. 6 is a coronal view of the vertebral body shown in FIG. 2, with a single tool shown in FIGS. 4 and 5 deployed through a posterolateral access in a collapsed condition.

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DETAILED DESCRIPTION OF THE PREFERRED EMBODIMENTS

This Specification describes new systems and methods to treat bones. The use of expandable bodies to treat bones is generally disclosed in U.S. Pat. Nos. 4,969,888 and 5,108,404, which are incorporated herein by reference. Improvements in this regard are disclosed in U.S. patent application, Ser. No. 08/188,224, filed Jan. 26, 1994; U.S. patent application Ser. No. 08/485,394, filed Jun. 7, 1995; and U.S. patent application Ser. No. 08/659,678, filed Jun. 5, 1996, which are each incorporated herein by reference. It should also be appreciated that the new systems and methods can be utilized to treat bones without use of expandable bodies, if desired.

The new systems and methods will be described with regard to the treatment of vertebral bodies. It should be appreciated, however, the systems and methods so described are not limited in their application to vertebrae. The systems and methods are applicable to the treatment of diverse bone types, including, but not limited to, such bones as the radius, the humerus, the femur, the tibia or the calcanus.

I. Vertebral Bodies

As FIG. 1 shows, the spinal column 10 comprises a number of uniquely shaped bones, called the vertebrae 12, a sacrum 14, and a coccyx 16(also called the tail bone). The number of vertebrae 12 that make up the spinal column 10 depends upon the species of animal. In a human (which FIG. 1 shows), there are twenty-four vertebrae 12, comprising seven cervical vertebrae 18, twelve thoracic vertebrae 20, and five lumbar vertebrae 22.

When viewed from the side, as FIG. 1 shows, the spinal column 10 forms an S-shaped curve. The curve serves to support the head, which is heavy. In four-footed animals, the curve of the spine is simpler.

As FIGS. 1 to 3 show, each vertebra 12 includes a vertebral body 26, which extends on the anterior (i.e., front or chest) side of the vertebra 12. As FIGS. 1 to 3 show, the vertebral body 26 is in the shape of an oval disk. As FIGS. 2 and 3 show, the vertebral body 26 includes an exterior formed from compact cortical bone 28. The cortical bone 28 encloses an interior volume 30 of reticulated cancellous, or spongy, bone 32(also called medullary bone or trabecular bone). A "cushion," called an intervertebral disk 34, is located between the vertebral bodies 26.

An opening, called the vertebral foramen 36, is located on the posterior (i.e., back) side of each vertebra 12. The spinal ganglion 39 pass through the foramen 36. The spinal cord 38 passes through the spinal canal 37.

The vertebral arch 40 surrounds the spinal canal 37. The pedicle 42 of the vertebral arch 40 adjoins the vertebral body 26. The spinous process 44 extends from the posterior of the vertebral arch 40, as do the left and right transverse processes 46.

II. Treatment of Vertebral Bodies

A. Lateral Access

Access to a vertebral body can be accomplished from many different directions, depending upon the targeted location within the vertebral body, the intervening anatomy, and the desired complexity of the procedure. For example, access can also be obtained through a pedicle 42 (transpedicular), outside of a pedicle (extrapedicular), along either side of the vertebral body (posterolateral), laterally or anteriorly. In addition, such approaches can be used with a closed, minimally invasive procedure or with an open procedure.

FIG. 4 shows a tool 48 for preventing or treating compression fracture or collapse of a vertebral body using an expandable body.

The tool 48 includes a catheter tube 50 having a proximal and a distal end, respectively 52 and 54. The distal end 54 carries a structure 56 having an expandable exterior wall 58. FIG. 4 shows the structure 56 with the wall 58 in a collapsed geometry. FIG. 5 shows the structure 56 in an expanded geometry.

The collapsed geometry permits insertion of the structure 56 into the interior volume 30 of a targeted vertebral body 26, as FIG. 6 shows. The structure 56 can be introduced into the interior volume 30 in various ways. FIG. 6 shows the insertion of the structure 56 through a single lateral access, which extends through a lateral side of the vertebral body 12.

Lateral access is indicated, for example, if a compression fracture has collapsed the vertebral body 26 below the plane of the pedicle 42, or for other reasons based upon the preference of the physician. Lateral access can be performed either with a closed, mininimally invasive procedure or with an open procedure. Of course, depending upon the intervening anatomy, well known in the art, lateral access may not be the optimal access path for treatment of vertebrae at all levels of the spine.

Figure 7:
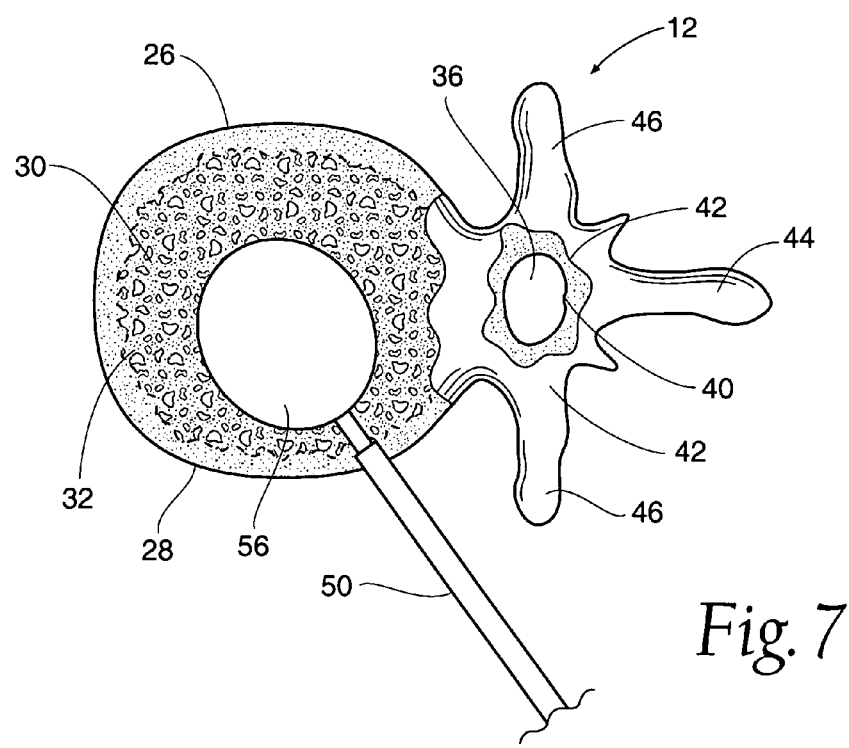
FIG. 7 is a coronal view of the vertebral body and tool shown in FIG. 6, with the tool in an expanded condition to compress cancellous bone and form a cavity.

The catheter tube 50 includes an interior lumen 80 (see FIG. 4). The lumen 80 is coupled at the proximal end of the catheter tube 50 to a pressurized source of fluid, e.g., saline. A syringe containing the fluid can comprise the pressure source. The lumen 80 conveys the fluid into the structure 56 under pressure. As a result, the wall 58 expands, as FIGS. 5 and 7 show.

The fluid is preferably rendered radio-opaque, to facilitate visualization as it enters the structure 56. For example, Renograffin™ can be used for this purpose. Because the fluid is radio-opaque, expansion of the structure 56 can be monitored fluoroscopically or under CT visualization. Using real time MRI, the structure 56 may be filled with sterile water, saline solution, or sugar solution, free of a radiopaque material. If desired, other types of visualization could be used, with the tool 48 carrying compatible reference markers. Alternatively, the structure could incorporate a radiopaque material within the material of the structure, or the structure could be painted or "dusted" with a radiopaque material.

Expansion of the wall 58 enlarges the structure 56, desirably compacting cancellous bone 32 within the interior volume 30 (see FIG. 7) and/or causing desired displacement of cortical bone. The compaction of cancellous bone 32 forms a cavity 60 in the interior volume 30 of the vertebral body 26 (see FIG. 8). As will be described later, a filling material 62 can be safely and easily introduced into the cavity 60 which the compacted cancellous bone 32 forms. In one embodiment, expansion of the structure 56 desirably forms a region of compacted cancellous bone which substantially surrounds the cavity 60. This region desirably comprises a physical barrier which limits leakage of the filling material 62 outside the vertebral body 26. In an alternate embodiment, the expansion of the structure 56 also desirably presses cancellous bone 32 into small fractures which may be present in cortical bone, thereby reducing the possibility of the filling material 62 exiting through the cortical wall. In another alternative embodiment, the expansion of the structure 56 desirably flattens veins in the vertebral body that pass through the cortical wall (e.g., the basivertebral vein), resulting in less opportunity for filling material 62 to extravazate outside the vertebral body through the veinous structure in the cortical wall.

Alternatively, expansion of the structure 56 will compress less dense and/or weaker regions of the cancellous bone, which desirably increases the average density and/or overall strength of the remaining cancellous bone.

The compaction of cancellous bone by the structure 56 can also exert interior force upon cortical bone. Alternatively, the structure 56 can directly contact the cortical bone, such that expansion and/or manipulation of the structure will cause displacement of the cortical bone. Expansion of the structure 56 within the vertebral body 26 thereby makes it possible to elevate or push broken and compressed bone back to or near its original prefracture position.

Figure 8:
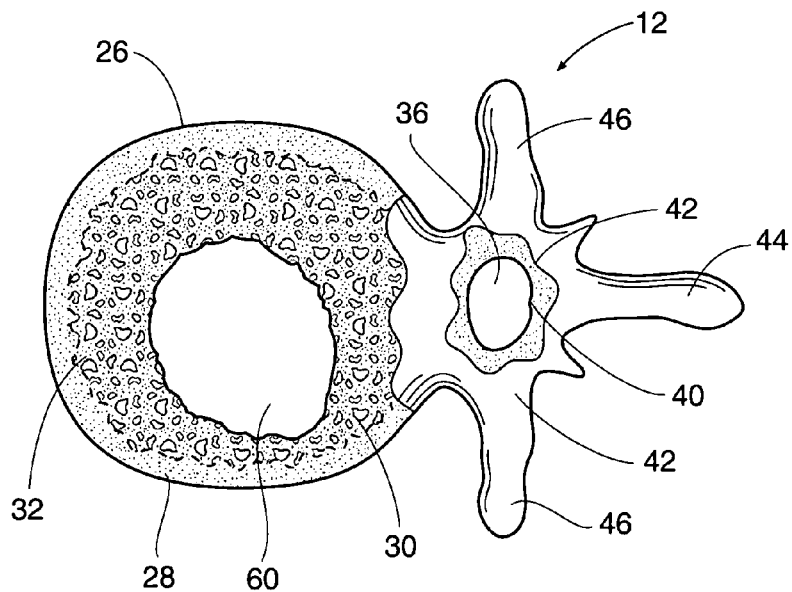
FIG. 8 is a coronal view of the vertebral body shown in FIGS. 6 and 7, with the tool removed after formation of the cavity.

The structure 56 is preferably left inflated within the vertebral body 26 for an appropriate waiting period, for example, three to five minutes, to allow some coagulation inside the vertebral body 26 to occur. After the appropriate waiting period, the physician collapses and removes the structure 56. As FIG. 8 shows, upon removal of the structure 56, the formed cavity 60 desirably remains in the interior volume 30.

Figure 9A:
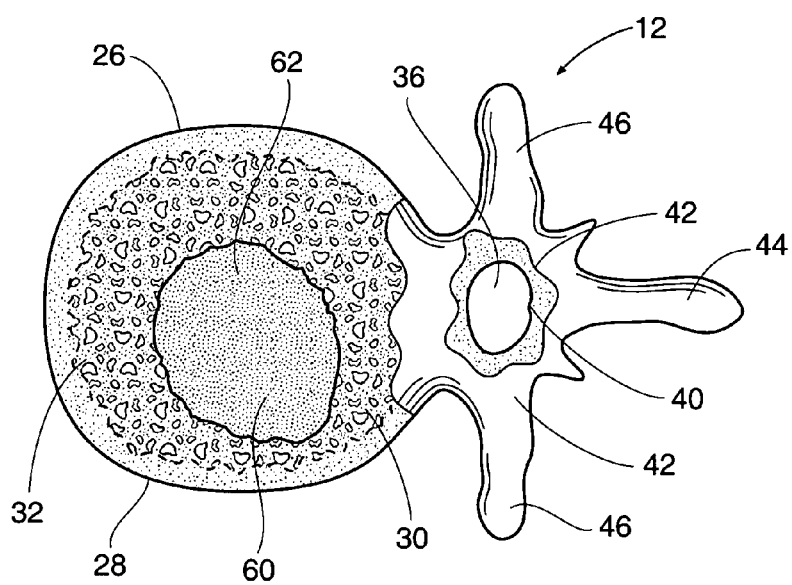
FIG. 9A is a coronal view of the vertebral body shown in FIG. 8, with the cavity filled with a material that strengthens the vertebral body.

As FIG. 9A shows, the physician next introduces a filling material 62 into the formed cavity 60. The filling material 62 can comprise a material that resists torsional, tensile, shear and/or compressive forces within the cavity 60, thereby providing renewed interior structural support for the cortical bone 28. For example, the material 62 can comprise a flowable material, such as bone cement, allograft tissue, autograft tissue, or hydroxyapatite, synthetic bone substitute, which is introduced into the cavity 60 and which, in time, sets to a generally hardened condition. The material 62 can also comprise a compression-resistant material, such as rubber, polyurethane, cyanoacrylate, or silicone rubber, which is inserted into the cavity 60. The material 62 can also comprise a semi-solid slurry material (e.g., a bone slurry in a saline base), which is either contained within a porous fabric structure located in the cavity 60 or injected directly into the cavity 60, to resist compressive forces within the cavity 60. Alternatively, the material 62 could comprise stents, reinforcing bar (Re-Bar) or other types of internal support structures, which desirably resist compressive, tensile, torsional and/or shear forces acting on the bone and/or filler material.

The filling material 62 may also comprise a medication, or a combination of medication and a compression-resistant material, as described above.

Alternatively, the filling material 62 can comprise a bone filling material which does not withstand compressive, tensile, torsional and/or shear forces within the cavity. For example, where the patient is not expected to experience significant forces within the spine immediately after surgery, such as where the patient is confined to bed rest or wears a brace, the filling material 62 need not be able to immediately bear loads. Rather, the filling material 62 could provide a scaffold for bone growth, or could comprise a material which facilitates or accelerates bone growth, allowing the bone to heal over a period of time. As another alternative, the filling material could comprise a resorbable or partially-resorbable source of organic or inorganic material for treatment of various bone or non-bone-related disorders including, but not limited to, osteoporosis, cancer, degenerative disk disease, heart disease, acquired immune deficiency syndrome (AIDS) or diabetes. In this way, the cavity and/or filler material could comprise a source of material for treatment of disorders located outside the treated bone.

In an alternative embodiment, following expansion, the expandable structure 56 can be left in the cavity 60. In this arrangement, flowable filling material 62 is conveyed into the structure 56, which serves to contain the material 62. The structure 56, filled with the material 62, serves to provide the renewed interior structural support function for the cortical bone 28.

In this embodiment, the structure 56 can be made from an inert, durable, non-degradable plastic material, e.g., polyethylene and other polymers. Alternatively, the structure 56 can be made from an inert, bio-absorbable material, which degrades over time for absorption or removal by the body.

In another embodiment, the filling material 62 itself can serve as the expansion medium for the structure 56, to compact cancellous bone and form the cavity 60, to thereby perform both compaction and interior support functions. Alternatively, the structure 56 can be first expanded with another medium to compact cancellous bone and form the cavity 60, and the filling material 62 can be subsequently introduced after the expansion medium is removed from structure 56 to provide the interior support function. As another alternative, the filling material could comprise a two-part material including, but not limited to, settable polymers or calcium alginate. If desired, one part of the filling material could be utilized as the expansion medium, and the second part added after the desired cavity size is achieved.

The structure 56 can be made from a permeable, semi-permeable, or porous material, which allows the transfer of medication contained in the filling material 62 into contact with cancellous bone through the wall of the structure 56. If desired, the material can comprise a membrane that allows osmotic and/or particulate transfer through the material, or the material can comprise a material that allows the medication to absorb into and/or diffuse through the material. Alternatively, medication can be transported through a porous wall material by creating a pressure differential across the wall of the structure 56.

As another alternative, fluids, cells and/or other materials from the patient's body can pass and/or be drawn through the material into the structure for various purposes including, but not limited to, fluid/cellular analysis, bony ingrowth, bone marrow harvesting, and/or gene therapy (including gene replacement therapy).

III. Instruments for Establishing Bone Access

During a typical bilateral procedure, a patient lies on an operating table. The patient can lie face down on the table, or on either side, or at an oblique angle, depending upon the physician's preference.

A. Use of Hand Held Instruments

Figure 10A:
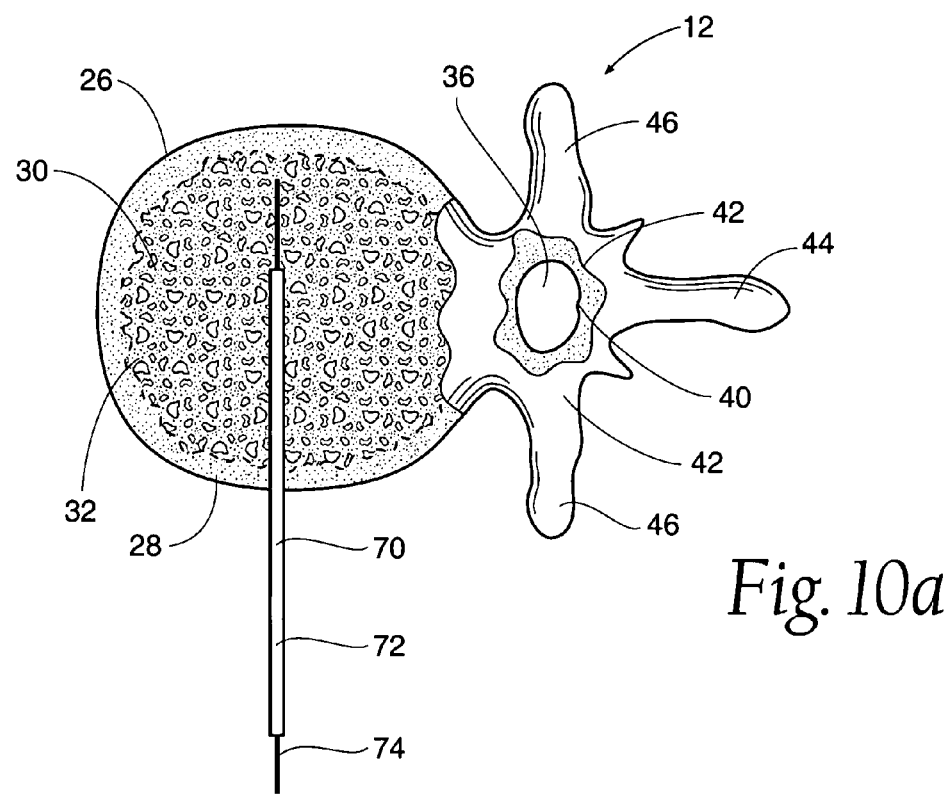
FIGS. 10A to 10I are coronal views of a vertebral body, showing tools deployed to create a posterolateral access to compress cancellous bone in a vertebral body to form an interior cavity, which is filled with a material to strengthen the vertebral body.

For each access (see FIG. 10A), the physician introduces a spinal needle assembly 70 into soft tissue ST in the patient's back. Under radiologic or CT monitoring, the physician advances the spinal needle assembly 70 through soft tissue down to and into the targeted vertebral body 26. The physician can also employ stereotactic instrumentation to guide advancement of the spinal needle assembly 70 and subsequent tools during the procedure. In this arrangement, the reference probe for stereotactic guidance can be inserted through soft tissue and implanted on the surface of the targeted vertebral body. The entire procedure can also be monitored using tools and tags made of non-ferrous materials, e.g., plastic or fiber composites, such as those disclosed in U.S. Pat. Nos. 5,782,764 and 5,744,958, which are each incorporated herein by reference, which would be suitable for use in a computer enhanced, whole-room MRI environment.

The physician will typically administer a local anesthetic, for example, lidocaine, through the assembly 70. In some cases, the physician may prefer other forms of anesthesia.

The physician directs the spinal needle assembly 70 to penetrate the cortical bone 28 and the cancellous bone 32 through the side of the vertebral body 26. Preferably the depth of penetration is about 60% to 95% of the vertebral body 26.

Figure 10B:
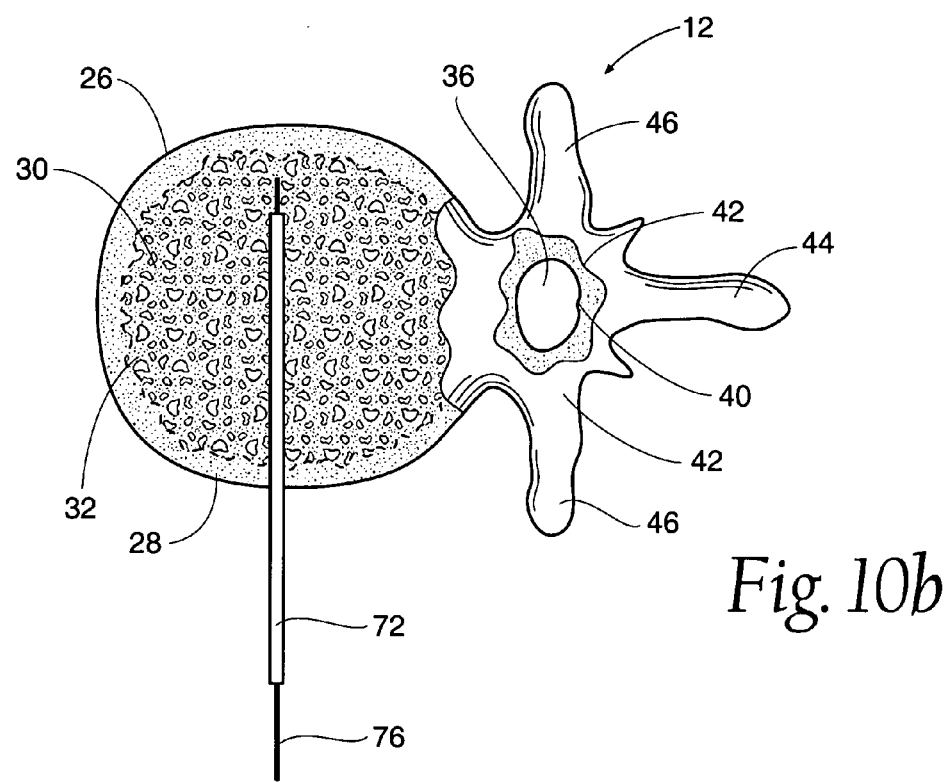

The physician holds the stylus 72 and withdraws the stylet 74 of the spinal needle assembly 70. As FIG. 10B shows, the physician then slides a guide pin instrument 76 through the stylus 72 and into the cancellous bone 32. The physician now removes the stylus 72, leaving the guide pin instrument 76 deployed within the cancellous bone 32.

Figure 10C:
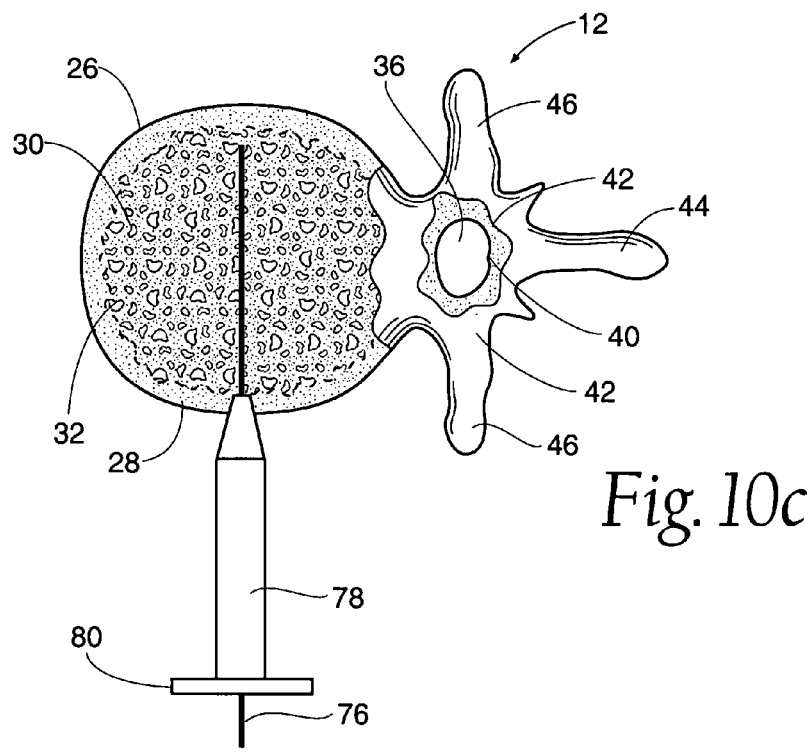

The physician next slides an obturator instrument 78 over the guide pin instrument 76, distal end first, as FIG. 10C shows. The physician can couple the obturator instrument 78 to a handle 80, which facilitates manipulation of the instrument 78.

The physician makes a small incision in the patient's back. The physician twists the handle 80 while applying longitudinal force to the handle 80. In response, the obturator instrument 78 rotates and penetrates soft tissue through the incision. The physician may also gently tap the handle 80, or otherwise apply appropriate additional longitudinal force to the handle 80, to advance the obturator instrument 78 through the soft tissue along the guide pin instrument 76 down to the cortical bone entry site. The physician can also tap the handle 80 with an appropriate striking tool to advance the obturator instrument 78 into a side of the vertebral body 26 to secure its position.

The obturator instrument 78 shown in FIG. 10C has an outside diameter that is generally well suited for establishing a lateral access. However, if access is desired through the more narrow region of the vertebral body 26, e.g., a pedicle 42 (called transpedicular access), the outside diameter of the obturator instrument 78 can be reduced. The reduced diameter of the obturator instrument 78 mediates against damage or breakage of the pedicle 42. It should be understood that the disclosed methods and devices are well suited for use in conjunction with other approach paths, such as pedicular, extra-pedicular, posterolateral and anterior approaches, with varying results.

The physician then proceeds to slide the handle 80 off the obturator instrument 78 and to slide a cannula instrument 84 over the guide pin instrument 76 and, further, over the obturator instrument 78. If desired, the physician can also couple the handle 80 to the cannula instrument 84, to apply appropriate twisting and longitudinal forces to rotate and advance the cannula instrument 84 through soft tissue ST over the obturator instrument 78. When the cannula instrument 84 contacts cortical bone 28, the physician can appropriately tap the handle 80 with a striking tool to advance the end surface into the side of the vertebral body 26 to secure its position.

The physician now withdraws the obturator instrument 78, sliding it off the guide pin instrument 76, leaving the guide pin instrument 76 and the cannula instrument 84 in place. When a reduced diameter obturator instrument 78 is used, the physician can remove an inner centering sleeve (not shown).

Figure 10D:
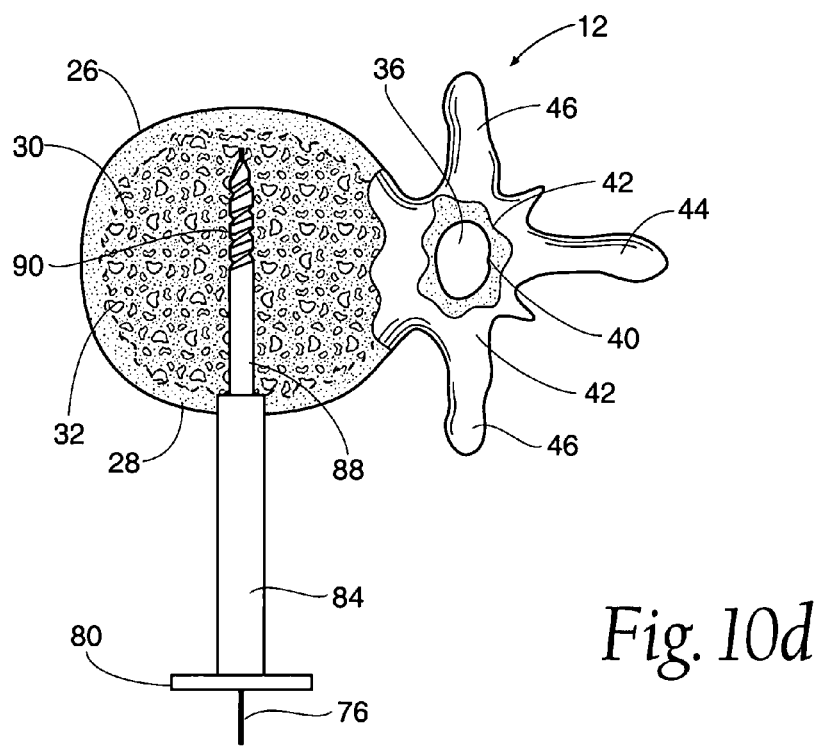

As FIG. 10D shows, the physician slides a drill bit instrument 88 over the guide pin instrument 76, distal end first, through the cannula instrument 84, until contact between the machined or cutting edge 90 of the drill bit instrument 88 and cortical bone 28 occurs. The physician then couples the drill bit instrument 88 to the handle 80.

Guided by X-ray (or another external visualizing system), the physician applies appropriate twisting and longitudinal forces to the handle 80, to rotate and advance the machined edge 90 of the drill bit instrument 88 to open a lateral passage PLA through the cortical bone 28 and into the cancellous bone 32. The drilled passage PLA preferably extends no more than 95% across the vertebral body 26.

Further details regarding the formation of cavities within cancellous bone, which are not symmetric with relation to the axis of a vertebral body, can be found in U.S. Pat. No. 5,972,018, entitled "Expandable Asymmetric Structures for Deployment in Interior Body Regions," which is incorporated herein by reference.

Figure 10E:
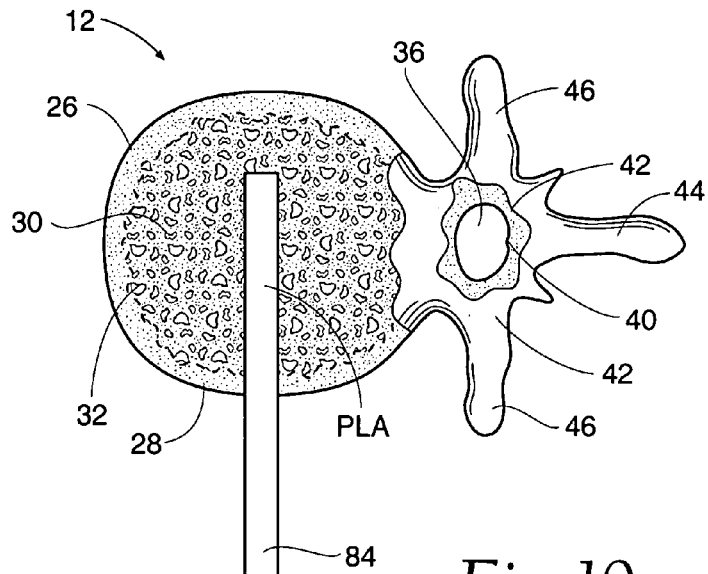
Figure 10F:
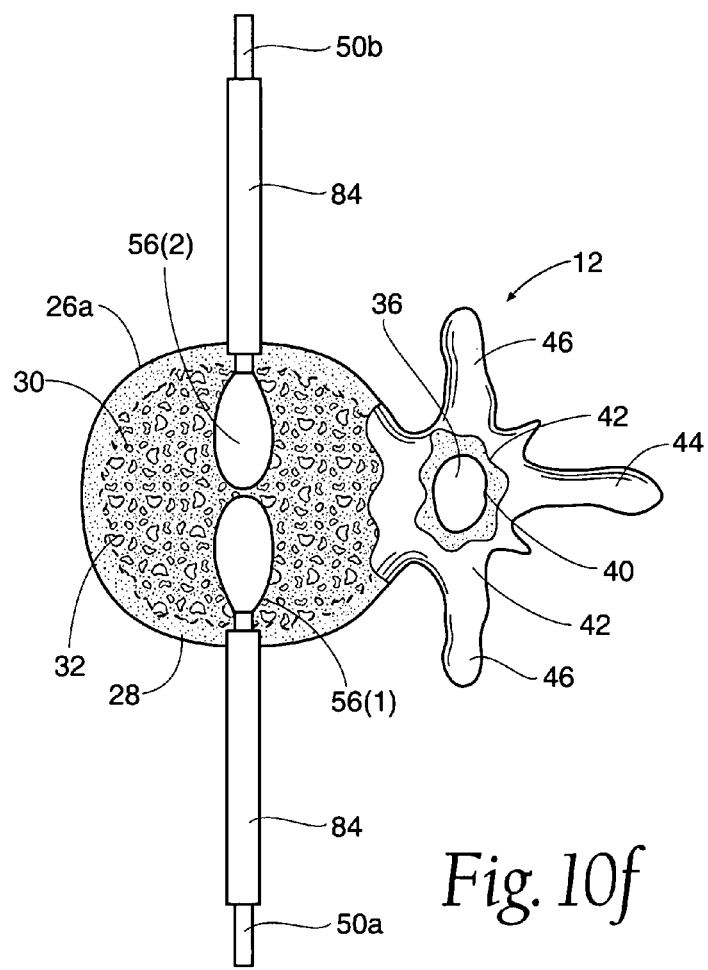
Figure 10G:
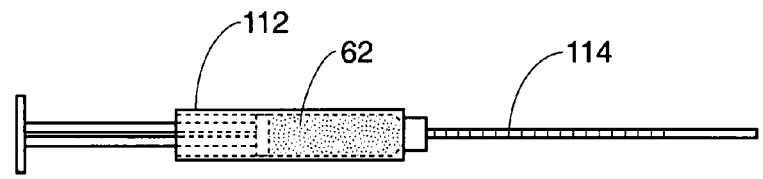

Once the passage PLA in cancellous bone 32 has been formed, the physician removes the drill bit instrument 88 and the guide pin instrument 76, leaving only the cannula instrument 84 in place, as FIG. 10E shows. The passage PLA made by the drill bit instrument 88 remains. Subcutaneous lateral access to the cancellous bone 32 has been accomplished.

If desired, other tools can be used to establish subcutaneous access to the targeted bone, such as the tools described in copending U.S. patent application Ser. No. 09/421,635, filed Oct. 19, 1999, and entitled "Hand-Held Instruments that Access Interior Body Regions," which is incorporated herein by reference.

B. Filling the Cavity

Upon formation of the cavity 64, the physician can fill a syringe 112 with the desired volume of filling material 62, a batch of which has been previously prepared. When using an expandable structure 56 having a preformed configuration, the cavity volume created is known. The physician thereby knows the desired volume of material 62 to place in the syringe 112 for each cavity formed in the vertebral body 26.

The physician attaches a nozzle 114 to the filled syringe 112. The physician then proceeds to deflate and remove the expandable structure through the associated cannula instrument 84 and to fill the associated cavity with the material 62.

Figure 10H:
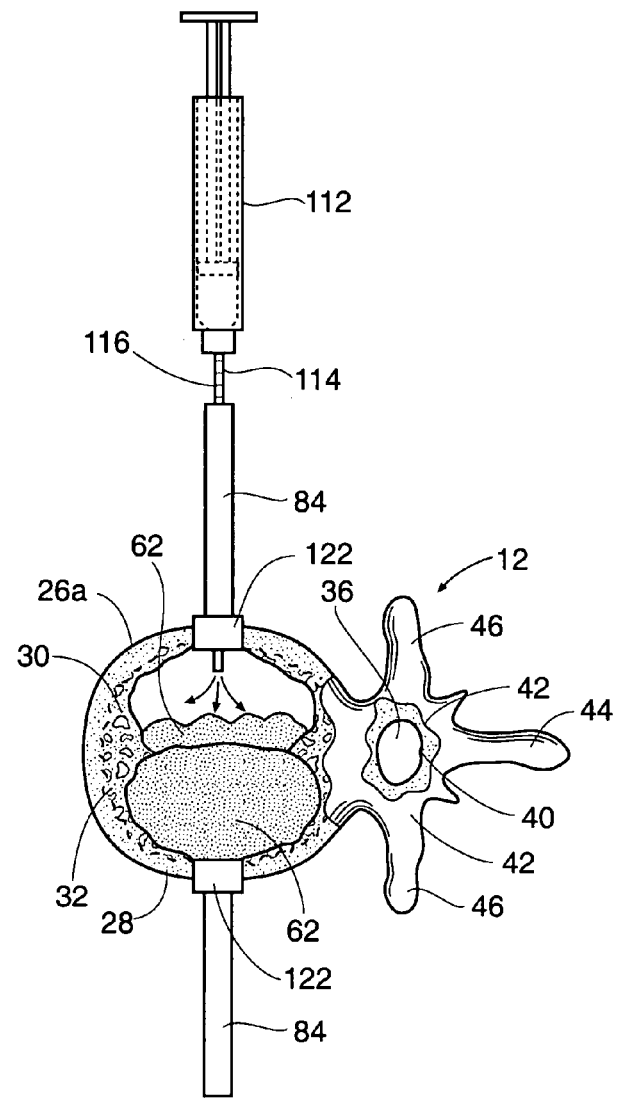

To fill the cavity, the physician inserts the nozzle 114 through the associated cannula instrument a selected distance into the cavity, guided, e.g., by exterior markings 116 or by real-time fluoroscope or x-ray or MRI visualization. The physician operates the syringe 112 to cause the material 62 to flow through and out of the nozzle 114 and into the cavity portion. As FIG. 10H shows, the nozzle 114 may posses a uniform interior diameter, sized to present a distal end dimension that facilitates insertion into the vertebral body. To reduce the overall flow resistance, however, the nozzle 114 can possess an interior diameter (e.g., see FIG. 11A) that steps down from a larger diameter at its proximal region 118 to a smaller diameter near its distal end 120. This reduces the average interior diameter of the nozzle 114 to thereby reduce the overall flow resistance. Reduced flow resistance permits more viscous material to be conveyed into the vertebral body. The more viscous material is desirable, because it has less tendency to exude from the bone compared to less viscous materials.

Figure 11A:
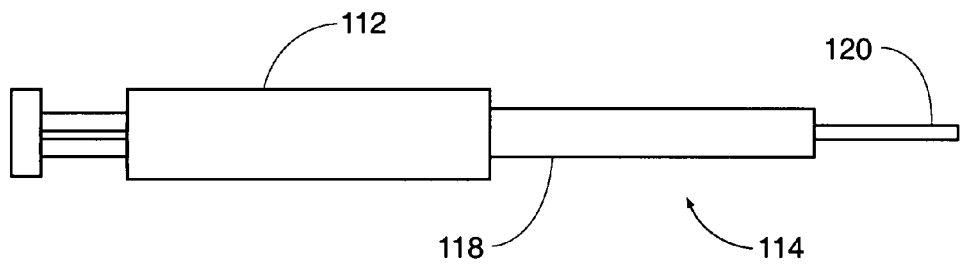
FIG. 11A is a side view of a tool to introduce material into a cavity formed in cancellous bone, with a nozzle having a stepped profile to reduce overall fluid resistance.
Figure 11B:
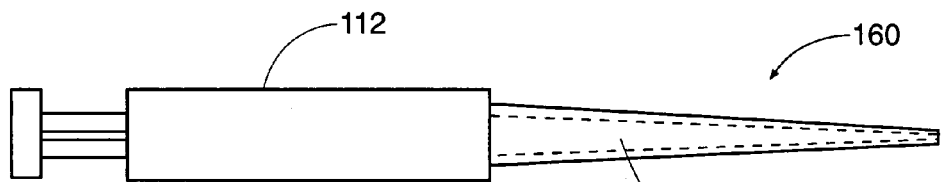
FIG. 11B is a side view of a tool to introduce material into a cavity formed in cancellous bone, with a nozzle having a tapered profile to reduce overall fluid resistance.
Figure 11C:
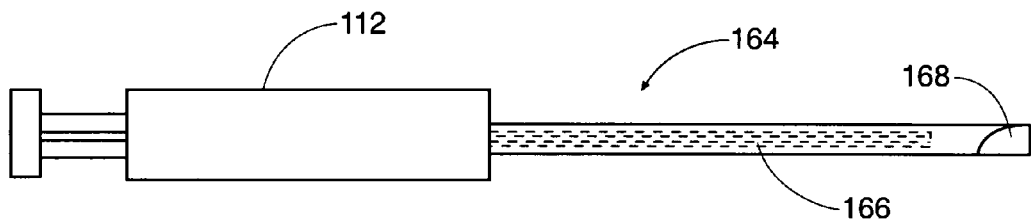
FIG. 11C is a side view of a tool to introduce material into a cavity formed in cancellous bone, with a nozzle having a reduced interior profile to reduce overall fluid resistance.

In addition to the embodiment shown in FIG. 11A, various other constructions are possible to create a reduced diameter nozzle or tool for introducing material into bone. For example, as shown in FIG. 11B, a tool 160 can possess an interior lumen 162 that gradually tapers from a larger interior diameter to a smaller interior diameter. Or, as shown in FIG. 11C, a tool 164 can possess an interior lumen 166 that steps from a larger to a smaller interior diameter. An associated cannula instrument 168 (see FIG. 11C) may also include a reduced diameter passage, which is downsized to accommodate the reduced diameter tool and to present less flow resistance to filling material conveyed through the cannula instrument.

The reduced diameter tool may also be used in association with a vertebroplasty procedure, which injects cement under pressure into a vertebral body, without prior formation of a cavity.

The filling material 62 may contain a predetermined amount of a radiopaque material, e.g., barium or tungsten, sufficient to enable visualization of the flow of material 62 into the cavity portion. The amount of radiopaque material (by weight) is desirably at least 10%, more desirably at least 20%, and most desirably at least 30%. The physician can thereby visualize the cavity filling process.

As material 62 fills the cavity portion, the physician withdraws the nozzle 114 from the cavity portion and into the cannula instrument 84. The cannula instrument 84 channels the material flow toward the cavity portion. The material flows in a stream into the cavity portion.

As FIG. 10H shows, a gasket 122 may be provided about the cannula instrument 84 to seal about the access passage PLA. The gasket 122 serves to prevent leakage of the material about the cannula instrument 84.

The physician operates the syringe 112 to expel the material 62 through the nozzle 114, first into the cavity portion and then into the cannula instrument 84. Typically, at the end of the syringe injection process, material 62 should extend from the cavity and occupy about 40% to 50% of the cannula instrument 84. Alternatively, the physician can utilize the syringe 112 to fill the lumen of the nozzle 114 and/or cannula instrument 84 with material 62, and then utilize a tamping instrument 124 to expel the material from the lumen into the vertebral body.

When a desired volume of material 62 is expelled from the syringe 112, the physician withdraws the nozzle 114 from the cannula instrument 84. The physician may first rotate the syringe 112 and nozzle 114, to break loose the material 62 in the nozzle 114 from the ejected bolus of material 62 occupying the cannula instrument 84.

Figure 10I:
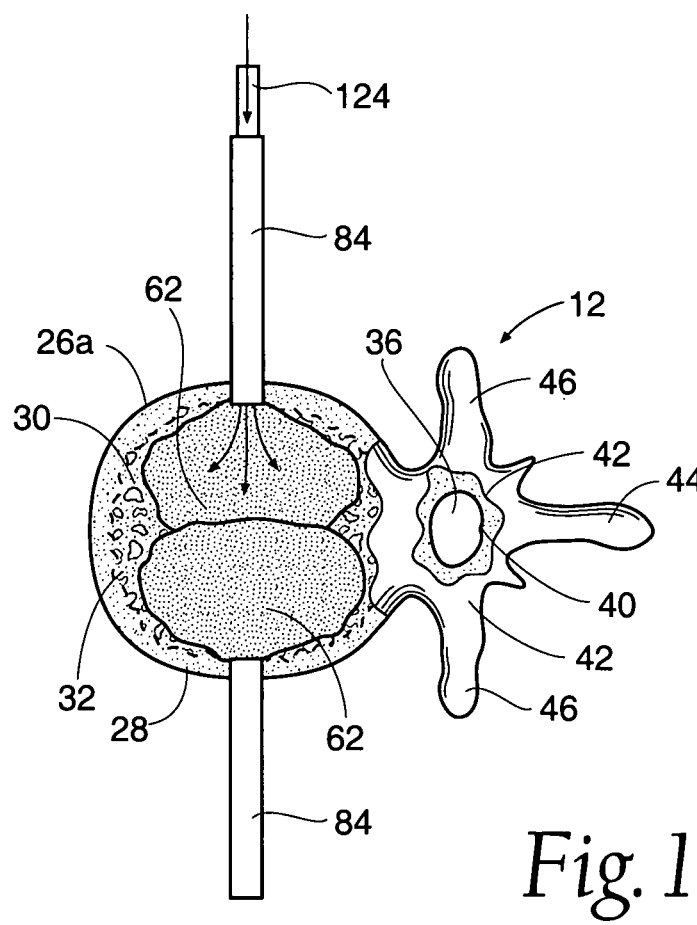

As FIG. 10I shows, the physician next advances a tamping instrument 124 through the cannula instrument 84. The distal end of the tamping instrument 124 contacts the residual volume of material 62 in the cannula instrument 84. Advancement of the tamping instrument 124 displaces progressively more of the residual material 62 from the cannula instrument 84, forcing it into the cavity portion. The flow of material 62 into the cavity portion, propelled by the advancement of the tamping instrument 124 in the cannula instrument 84, serves to uniformly distribute and compact the material 62 inside the cavity portion, into other cavities and/or openings within the bone, and into fracture lines, without the application of extremely high pressure.

The use of the syringe 112, nozzle 114, and the tamping instrument 124 allows the physician to exert precise control when filling the cavity portion with material 62. The physician can immediately adjust the volume and rate of delivery according to the particular local physiological conditions encountered. The application of low pressure, which is uniformly applied by the syringe 112 and the tamping instrument 124, allows the physician to respond to fill volume and flow resistance conditions in a virtually instantaneous fashion. The chance of overfilling and leakage of material 62 outside the cavity portion is significantly reduced.

Figure 12:
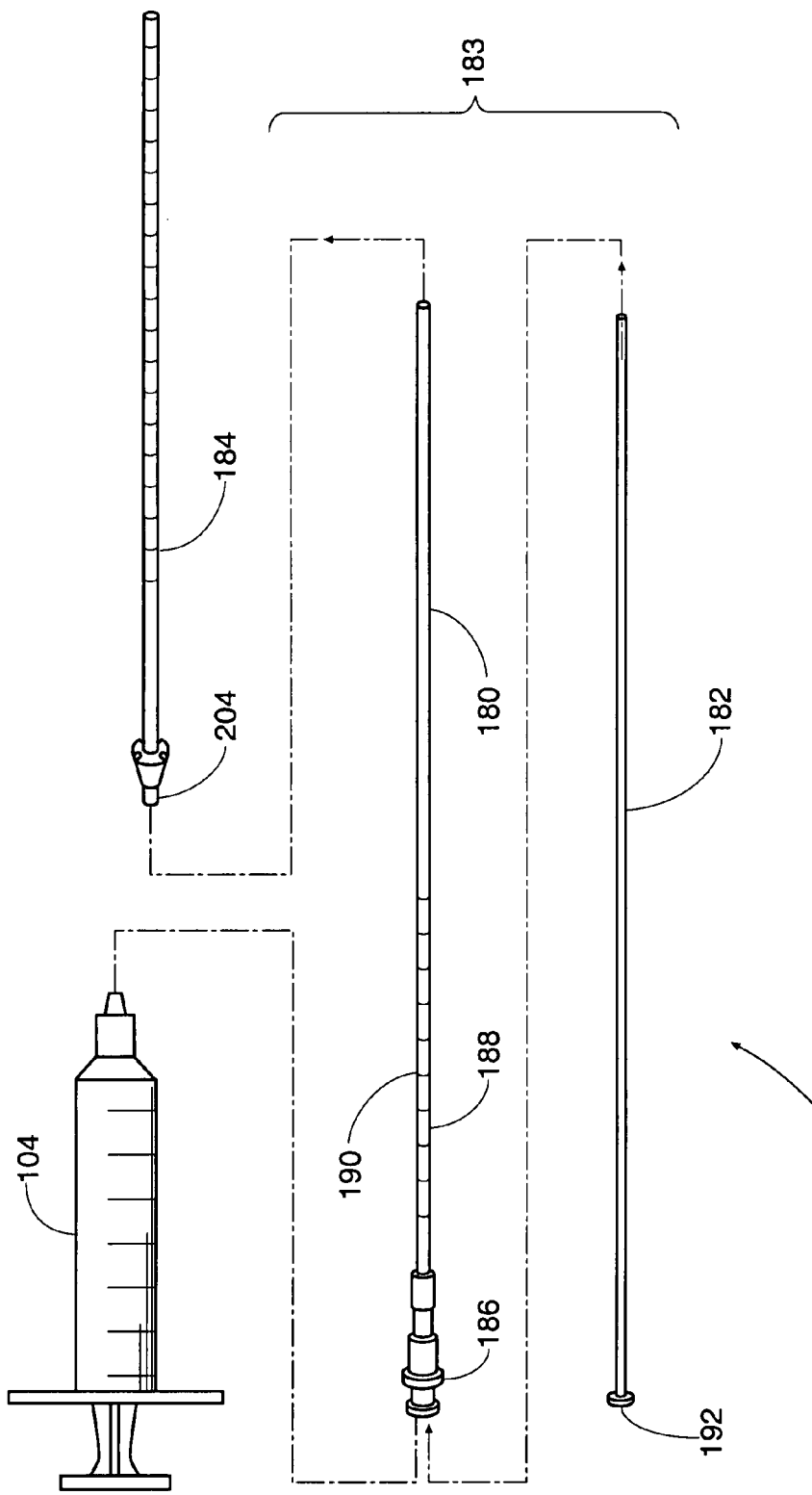
FIG. 12 is an exploded perspective view of a cannula and material introducing device, which embodies features of the invention.

Moreover, the tamping instrument 124 will desirably permit highly-controlled injection of material 62 under higher injection pressures as well. For example, FIG. 12 depicts a material injection instrument 500 comprising a reduced diameter nozzle 180 and a stylet 182. The stylet 182 is desirably sized to pass through the reduced diameter nozzle 180. In turn, the nozzle 180 is desirably sized to pass through the cannula instrument 184. For material strength, the nozzle 180 can be formed from a substantially rigid metal material, e.g., stainless steel or a high strength plastic.

The stylet 182 includes a handle 192, which rests on the proximal connector 186 of the nozzle when the stylet 182 is fully inserted into the nozzle 180. When the handle is rested, the distal ends of the stylet 182 and nozzle 180 align. The presence of the stylet 182 inside the nozzle 180 desirably closes the interior bore.

In use, the nozzle 180 can be coupled to the syringe 104 and inserted through the cannula instrument 184 into a material-receiving cavity (not shown) formed within a bone. Material 62 in the syringe 104 is injected into the nozzle 180 where it desirably passes into the bone. When a sufficient amount of material 62 is injected into the bone and/or nozzle 180, the syringe 104 may be removed from the nozzle 180.

The stylet 182 can then be inserted into the nozzle 180, and advanced through the nozzle, desirably pressurizing the material 62 and pushing it out of the nozzle 180. In one disclosed embodiment, the stylet 182 has a diameter of approximately 0.118 in. The cross-sectional area of this stylet 182 is approximately 0.010936 in$^2$, and the nozzle 180 desirably contains approximately 1.5 cc of filler material. In this embodiment, pushing the stylet 182 into the nozzle 180 with a force of force of ten (10) pounds can produce a pressure of approximately 914 lb-in$^2$ in the filler material 62 within the nozzle 180. In an alternate embodiment, the stylet 182 has a diameter of approximately 0.136 in. A force of ten (10) pounds utilized on this stylet can produce a pressure of approximately 688 lb-in$^2$ in the filler material 62 within the nozzle 180.

The nozzle 180 and stylet 182 can be used in a similar manner as a combination ram 183 to push the filler material 62 through the cannula instrument 184 into the bone. For example, where filler material 62 is within the cannula instrument 184, the insertion of the ram 183 into the cannula 184 will desirably displace the material 62, forcing the material 62 from the distal end of the cannula 184 into the bone. In one embodiment, the diameter of the ram 183 is approximately 0.143 in. In this embodiment, pushing the ram 183 with a force of ten (10) pounds is capable of producing a pressure of 622 lb-in$^2$ in the filler material 62 within the cannula 184. As the ram 183 advances through the cannula 184, it will desirably displace the filler material 62 in the cannula 184. The ram 183, therefore, acts as a positive displacement "piston" or "pump," which permits the physician to accurately gauge the precise amount of filler material 62 that is injected into the bone.

If the filler material is very viscous, this material will typically strongly resist being pumped through a delivery system. Generally, the greater distance the filler material must travel through the system, the greater the pressure losses will be from such factors as viscosity of the material and frictional losses with the walls. In order to account for these losses, existing delivery systems typically highly pressurize the filler material, often to many thousands of pounds of pressure. Not only does this require stronger pumps and reinforced fittings for the delivery system, but such systems often cannot dispense filler material in very precise amounts. Moreover, if the filler material hardens over time, the system must produce even greater pressures to overcome the increased flow resistance of the material.

The disclosed systems and methods obviate and/or reduce the need for complex, high pressure injection systems for delivery of filler materials. Because the disclosed ram 183 travels subcutaneously through the cannula 184, and displaces filler material 62 out the distal end of the cannula 184, the amount of filler material being pushed by the ram 183 (and the total amount of filler material 62 within the cannula 184) progressively decreases as filler material is injected into the bone. This desirably results in an overall decrease in resistance to movement of the ram during injection. Moreover, because the amount of material being "pushed" by the ram 183 decreases, an increase in the flow resistance of the curing filler material does not necessarily require an increase in injection pressure. In addition, because the ram 183 travels within the cannula 184, and can travel percutaneously to the injection site, the filler material need only be "pumped" a short length before it exits the cannula and enters the bone, further reducing the need for extremely high pressures. If injection of additional filler material is required, the ram can be withdrawn from the cannula, additional filler material can be introduced into the cannula, and the process repeated. Thus, the present arrangement facilitates injection of even extremely viscous materials under well controlled conditions. Moreover, by utilizing varying diameters of cannulas, nozzles and stylets in this manner, a wide range of pressures can be generated in the filler material 62. If desired, the disclosed devices could similarly be used to inject filler material through a spinal needle assembly directly into bone, in a vertebroplasty-like procedure, or can be used to fill a cavity created within the bone.

If desired, after the physician has filled the cavity with material 62, the physician may choose to continue injecting additional material 62 into the vertebral body. Depending upon the local conditions within the bone, this additional material may merely increase the volume of the cavity (by further compacting cancellous bone), or may travel into the compressed and/or uncompressed cancellous bone surrounding the cavity, which may serve to further compress cancellous bone and/or further enhance the compressive strength of the vertebral body.

When the physician is satisfied that the material 62 has been amply distributed inside the cavity portion, the physician withdraws the tamping instrument 124 from the cannula instrument 84. The physician preferably first twists the tamping instrument 124 to cleanly break contact with the material 62.

Once the cavity is filled and tamped in the above described manner, the cannula instrument 84 can be withdrawn and the incision site sutured closed.

Eventually the material 62, if cement, will harden to a rigid state within the cavity 64. The capability of the vertebral body to withstand loads has thereby been improved.

Figure 9B:
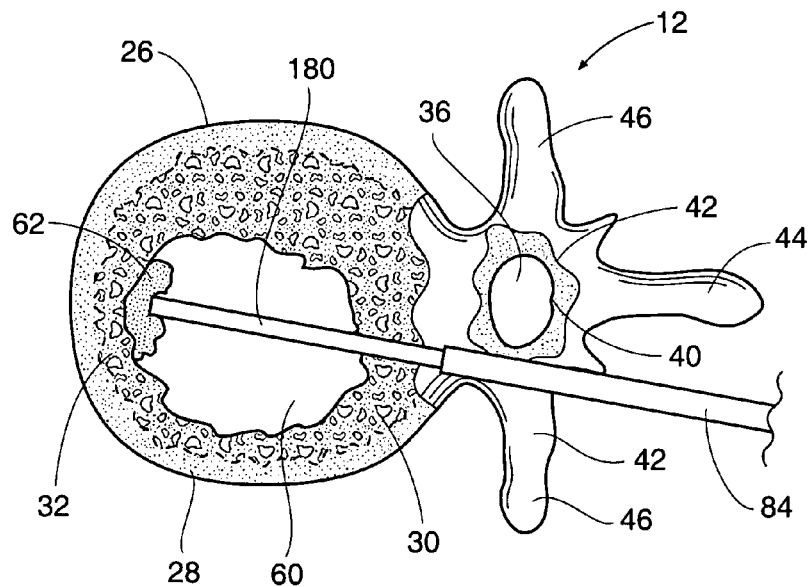
FIG. 9B depicts an alternate method of filling a cavity within a vertebral body.
Figure 9C:
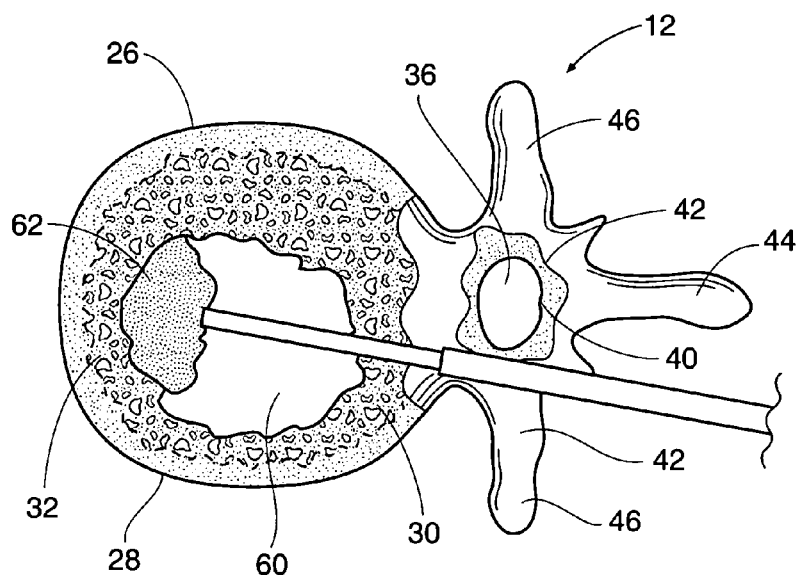
FIG. 9C depicts the vertebral body of FIG. 9B, wherein the cavity is approximately half-filled with material.
Figure 9D:
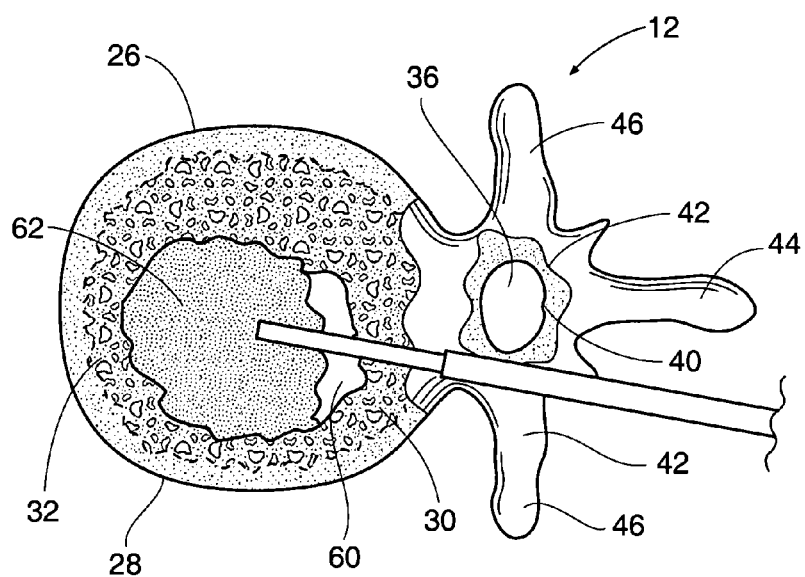
FIG. 9D depicts the vertebral body of FIG. 9B, wherein the cavity is substantially filled with material.

FIGS. 9B through 9D depict an alternate method of filling a cavity 60 formed within a vertebral body. In this embodiment, a cannula instrument 84 has been advanced through a pedicle 42 of the vertebral body by, providing access to a cavity 60 formed therein. A nozzle 180 is advanced into the vertebral body, with the distal tip of the nozzle 180 desirably positioned near the anterior side of the cavity 60. Filler material 62 is slowly injected through the nozzle 180 into the cavity 60. As injection of filler material 62 continues, the nozzle 180 is withdrawn towards the center of the cavity 60. See FIG. 9c. Desirably, as the nozzle 180 is withdrawn, the distal tip of the nozzle 180 will remain substantially in contact with the growing bolus of filler material 62. Once the nozzle 180 is positioned near the center of the cavity 60, additional filler material 62 is injected through the nozzle 180 to substantially fill the cavity 60. The nozzle is then removed from the cavity 60.

If desired, the nozzle can be attached to a syringe 104 (see FIG. 12) containing filler material. In one embodiment, the syringe 104 will contain an amount of filler material equal to the volume of the cavity 60 formed within the vertebral body, with the nozzle containing an additional 1.5 cc of filler material. In this embodiment, the cavity 60 will initially be filled with filler material expelled from the syringe 104. Once exhausted, the syringe 104 can be removed from the nozzle 180, a stylet 182 inserted into the nozzle 180, and the remaining filler material within the nozzle 180 pushed by the stylet 182 into the vertebral body. Desirably, the additional filler material from the nozzle 180 will extravazate into the cancellous bone, compress additional cancellous bone and/or slightly increase the size of the cavity 60.

The disclosed method desirably ensures that the cavity is completely filled with filler material. Because the patient is often positioned front side (anterior side) down during the disclosed procedures, the anterior section of the cavity is often the lowest point of the cavity. By initially filling the anterior section of the cavity with filler material, and then filling towards the posterior side of the cavity, fluids and/or suspended solids within the cavity are desirably displaced by the filler material and directed towards the posterior section of the cavity, where they can exit out the cannula. In this manner, "trapping" of fluids within the cavity and/or filler material is avoided and a complete and adequate fill of the vertebral body is ensured.

If desired, the filler material can be allowed to harden and/or cure before injection into the vertebral body. For example, in one embodiment, the filler material comprises bone cement, which is allowed to cure to a glue or putty-like state before being injected into the cavity. In this embodiment, the cement would desirably have a consistency similar to toothpaste as the cement begins to extrude from the nozzle.

The selected material 62 can also be an autograft or allograft bone graft tissue collected in conventional ways, e.g., in paste form (see Dick, "Use of the Acetabular Reamer to Harvest Autogenic Bone Graft Material: A Simple Method for Producing Bone Paste," *Archives of Orthopaedic and Traumatic Surgery* (1986), 105: 235-238), or in pellet form (see Bhan et al, "Percutaneous Bone Grafting for Nonunion and Delayed Union of Fractures of the Tibial Shaft," *International Orthopaedics (SICOT)* (1993) 17: 310-312). Alternatively, the bone graft tissue can be obtained using a Bone Graft Harvester, which is commercially available from SpineTech. Using a funnel, the paste or pellet graft tissue material is loaded into the cannula instrument 84 30. The tamping instrument 124 is then advanced into the cannula instrument 84 in the manner previously described, to displace the paste or pellet graft tissue material out of the cannula instrument 84 and into the cavity portion.

The selected material 62 can also comprise a granular bone material harvested from coral, e.g., ProOsteon™ calcium carbonate granules, available from Interpore. The granules are loaded into the cannula instrument 84 using a funnel and advanced into the cavity using the tamping instrument 124.

The selected material 62 can also comprise demineralized bone matrix suspended in glycerol (e.g., Grafton™ allograft material available from Osteotech), or SRS™ calcium phosphate cement available from Norian. These viscous materials, like the bone cement previously described, can be loaded into the syringe 112 and injected into the cavity using the nozzle 114, which is inserted through the cannula instrument 84 into the cavity portion. The tamping instrument 124 is used to displace residual material from the cannula instrument 84 into the cavity portion, as before described.

The selected material 62 can also be in sheet form, e.g. Collagraft™ material made from calcium carbonate powder and collagen from bovine bone. The sheet can be rolled into a tube and loaded by hand into the cannula instrument 84. The tamping instrument 124 is then advanced through the cannula instrument 84, to push and compact the material in the cavity portion.

C. Multi-Stage Injection Instruments

Figure 13B:
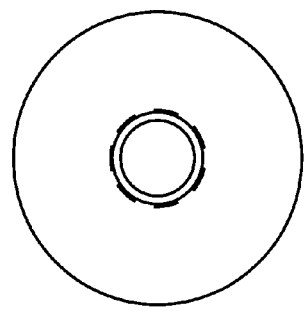
FIG. 13B is a side view of the filler instrument of FIG. 13A, taken along line 13B-13B.
Figure 13A:
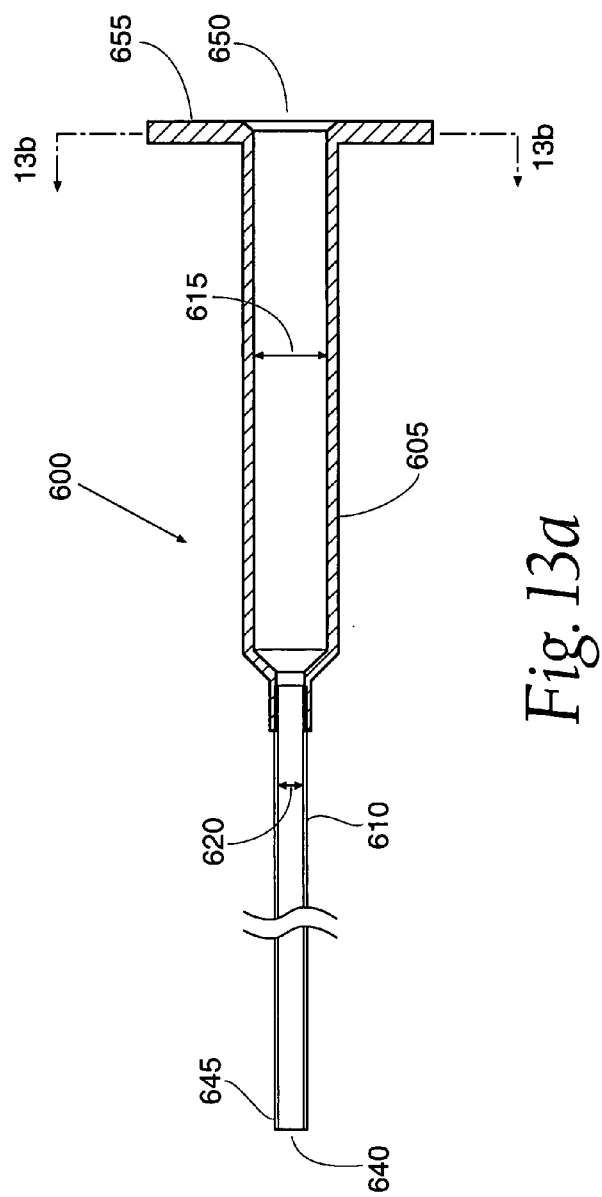
FIG. 13A is a cross-sectional side view of one embodiment of a filler instrument constructed in accordance with the teachings of the present invention.
Figure 14C:
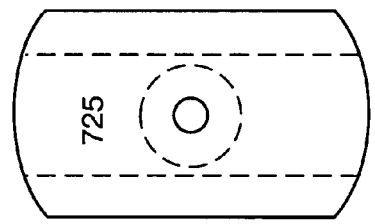
FIGS. 14B and 14C are side views of the first ram assembly of FIG. 14A.
Figure 14B:
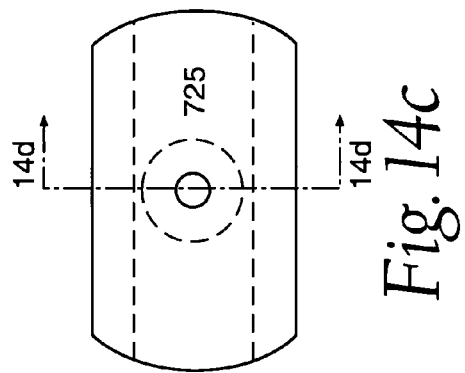
Figure 14D:
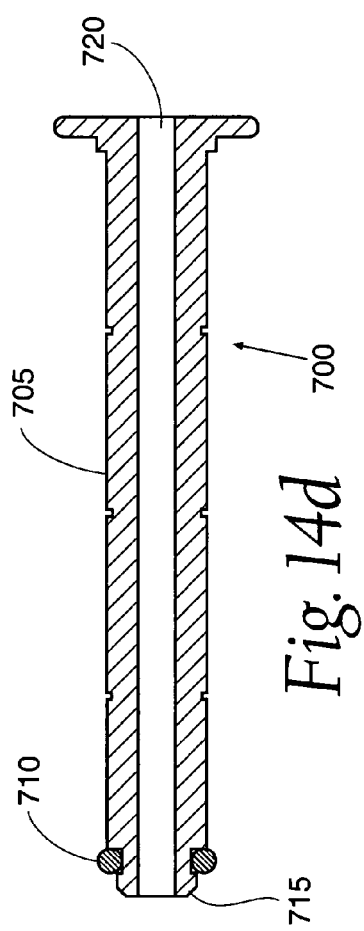
FIG. 14D is a cross-sectional view of the first ram assembly of FIG. 14C, taken along line 14D-14D.
Figure 14A:
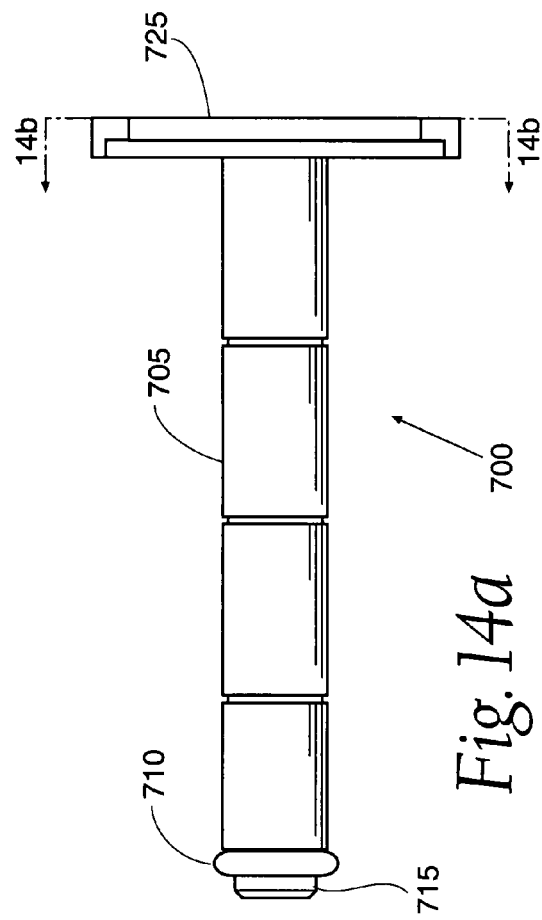
FIG. 14A is a side view of one embodiment of a first ram assembly constructed in accordance with the teachings of the present invention.

FIGS. 13A and 13B depict one embodiment of a filler instrument for introducing a desired amount of filling material into a bone or other vertebral body. Filler instrument 600 comprises a first section 605 and a second section 610. The first and second sections 605 and 610 are desirably hollow tubular bodies connected and/or secured in a sealing relationship, with the interior of the first section 605 being in fluid communication with the interior of the second section 610.

The first section 605 has a first interior cross-sectional area 615, and the second section 610 has a second interior cross-sectional area 620. Desirably, the first interior cross-sectional area 615 will be greater than the second interior cross-sectional area 620. In the disclosed embodiment, the first section 605 comprises a cylindrical, hollow, tubular member having an interior diameter of 0.358 inches and a length of 2.58 inches, and the second section comprises a cylindrical, hollow, tubular member having an interior diameter of 0.175 inches and a length of 8.84 inches.

A dispensing opening 640 is formed at the distal tip 645 of the second section 610. A first ram opening 650 is formed at the proximal end of the first section 605. If desired, a flange 655 can be formed on the outer portion of the first section 605. If also desired, the transition from the first section 605 to the second section 610 can neck down or taper, as shown in FIG. 13A.

FIGS. 14A through 14D depict a first ram assembly 700 suitable for use with the described filler instrument 600. The first ram assembly 700 comprises a first plunger 705 sized to pass through the interior of the first section 605. A seal 710, such as an O-ring, is secured to the distal end 715 of the first plunger 705 in a manner well known in the art. Desirably, the seal 710 will slidingly engage with the inner walls of the first section 605 to seal the proximal end of the first section 605 as the first plunger 705 advances therethrough. Desirably, the seal 710 will comprise Teflon, natural rubber, or other type of sealant material. It should be noted that, while the cross-section of the disclosed plunger is circular (see FIG. 14B), plungers having other cross-sectional shapes, such as triangular or rectangular shapes, could similarly be utilized with varying results.

If desired, a ram flange 725 can be formed on the distal portion of the first plunger 705. Desirably, the ram flange 725 will abut and/or contact the flange 655 when the distal end of the first plunger 705 reaches a desired position near or abutting the distal end of the first section 605. The first ram assembly 700 further comprises a second ram opening 720 extending longitudinally through the first plunger 705. Desirably, the size and shape of the cross-sectional area of the second ram opening 720 will be less than or approximate the size and shape of the second interior cross-sectional area 620. In the disclosed embodiment, the first ram assembly 700 is 2.62 inches long, the first plunger 705 having an outer diameter of 0.357 inches, and the inner diameter of the second ram opening 720 is 0.115 inches.

Figure 16A:
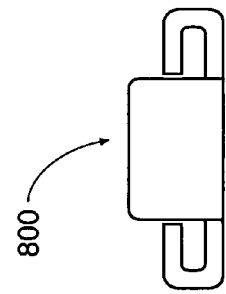
FIGS. 16A through 16C are views of a clip assembly.
Figure 16B:
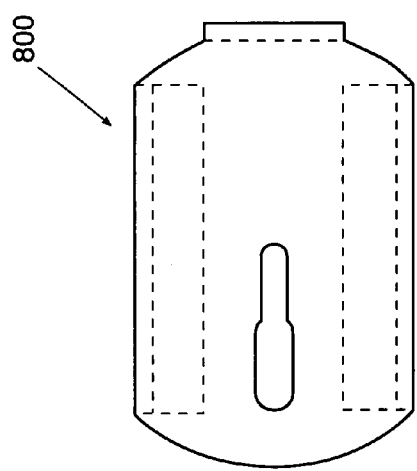
Figure 16C:
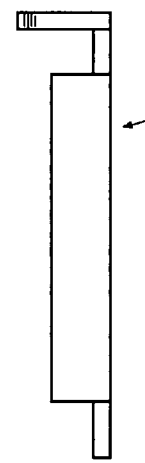
Figure 18:
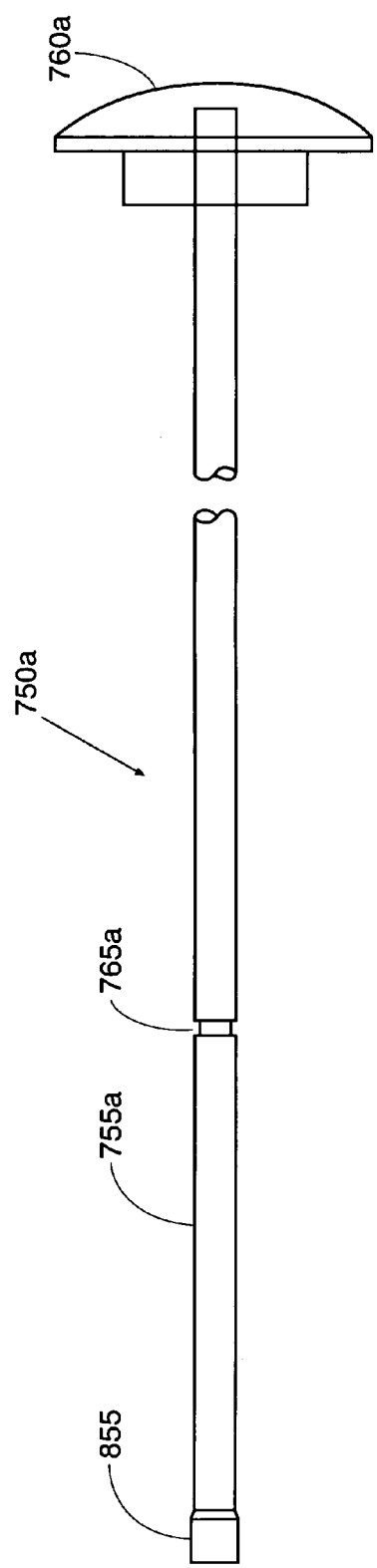
FIG. 18 is a side view of an alternate embodiment of a second ram assembly constructed in accordance with the teachings of the present invention.
Figure 19D:
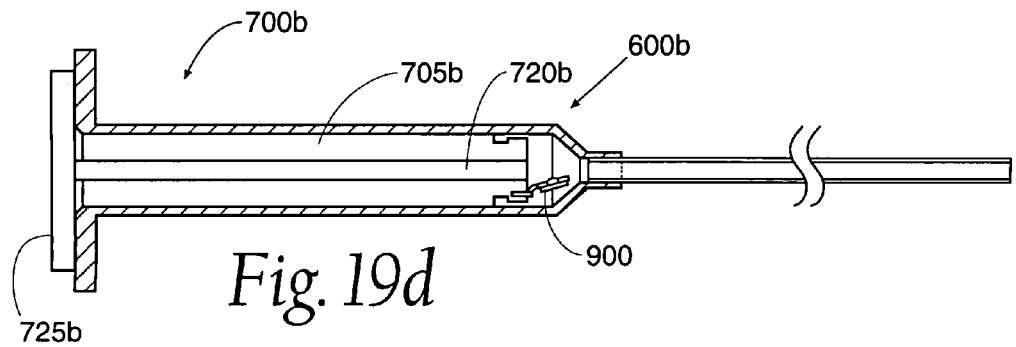
FIGS. 19A through 19D are views of another alternate embodiment of a first ram assembly and filler instrument constructed in accordance with the teachings of the present invention.
Figure 19C:
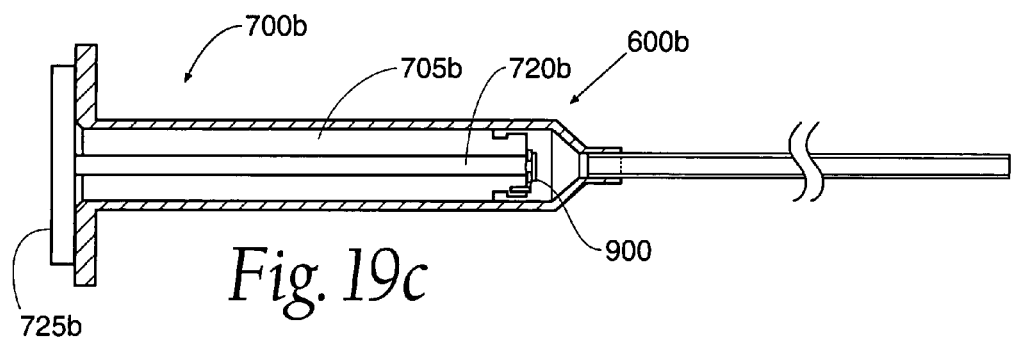
Figure 19B:
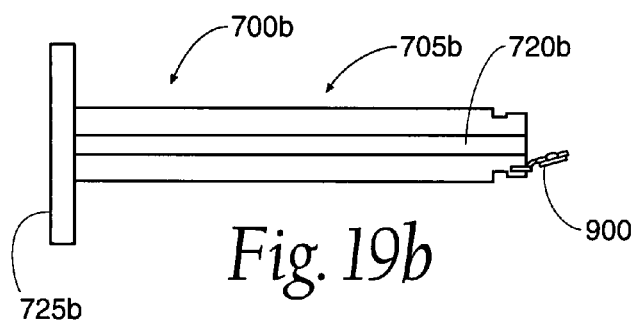
Figure 19A:
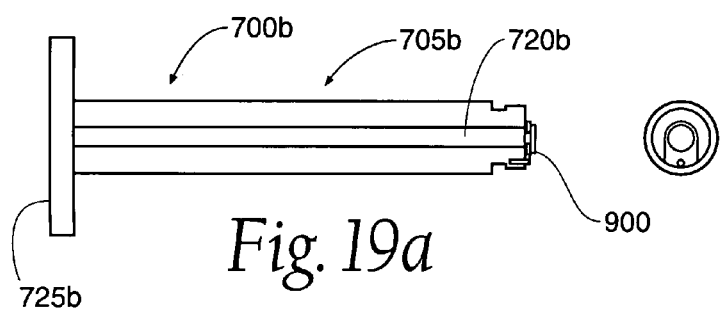

FIG. 15 depicts a second ram assembly 750 suitable for use with the first ram assembly 700 and the filler instrument 600. The second ram assembly 750 comprises a second plunger 755, and a knob 760 secured to the proximal end of the second plunger 755. The second plunger 755 is desirably sized to pass through the second ram opening 720 and the second section 610. In one embodiment, the second ram assembly further comprises a notch 765. A retaining clip 800 (see FIGS. 16A through 16C) desirably releasably secures the second ram assembly 750 within the second ram opening 720. In the disclosed embodiment, the second ram assembly 750 is 11.8 inches long, the second plunger 755 has an outer diameter of 0.113 inches, and the notch 765 is located approximately 2.62 inches from the distal tip of the second plunger 755.

For material strength, the various components of the filler instrument 600 can comprise a substantially rigid metal, plastic or ceramic material, e.g., stainless steel or a high strength plastic. In the disclosed embodiment, the filler instrument 600 and second ram assembly comprise 303 stainless steel, and the first ram assembly comprises Delrin® plastic (available commercially from DuPont Corporation).

When injection of filler material is desired, the filler instrument 600 is filled with filler material (not shown) such as bone cement or PMMA. The second ram assembly 750 is secured within the first ram assembly with the retaining clip 800. The distal end 715 of the first plunger 705 is then inserted into the first ram opening 650.

As the first plunger 705 is advanced through the first section 605 of the filler instrument 600, filler material in the first section 605 is displaced by the plunger 705, which in turn forces material in the second section 610 out through the dispensing opening 640. Passage of a significant amount of filler material through the second ram opening 720 is prevented by the presence of the second plunger 755, which is desirably held in position by the retaining clip 800. As the distal end 715 approaches the distal end of the first section 605, desirably substantially all of the filler material will be displaced from the first section 605 into the second section 610 and/or out the dispensing opening 640.

The retaining clip 800 is then released, and the second plunger 755 advanced through the distal end of the first section 605 and into the second section 610. Desirably, the shape and size of the cross-sectional area of the second plunger 755 will approximate the shape and size of the cross-sectional area 620 of the second section 610, such that the second plunger 755 displaces substantially all of the filler material in the second section 610 as the second plunger 755 advances. Desirably, once the distal end of the second plunger 755 reaches the dispensing opening 640, substantially all of the filler material within the first and second sections 605 and 610 will be dispensed from the filler instrument 600.

By utilizing first and second sections of different cross-sectional areas, and first and second plungers to displace the filler material, the present invention facilitates dispensing of a substantial amount of filler material from a single filler instrument. Because the viscosity of PMMA and various other types of filler materials typically increases with time during the dispensing process, it becomes progressively harder to dispense filler material over time. By utilizing a plunger of larger cross-sectional area to initiate the filling operation, when the filler material is less viscous, the present invention allows dispensing of a significant amount of filler material. However, as the filler material cures, and becomes more viscous, the reduced cross-sectional area of the second plunger allows continued dispensing of the more viscous filler material, even when it is in a highly viscous state. Moreover, because the second section is of reduced cross-sectional area, its reduced profile will desirably allow the distal tip of the filler instrument to be introduced through the cannula and/or soft tissues and directly into the targeted vertebral body, while still providing a sufficient reservoir of filler material to accomplish the goals of augmenting and/or repairing the targeted bone. Moreover, because the tool need not be refilled and/or "switched out" during the dispensing operation, but can rather remain in place and dispense the entire required amount of bone filler for the procedure, the potential for trapping air within the vertebral body and/or bolus of cement is significantly reduced.

The present invention also greatly facilitates the ability of the physician to immediately shift from a higher volume, lower pressure cement flow to a lower volume, higher pressure cement flow. As the first plunger is being depressed, and cement is being injected into the vertebral body, the physician may determine that a more controlled, higher pressure and/or lower volume flow of cement is needed. Alternatively, the cement may cure or harden to a point where further movement of the first plunger is extremely difficult and/or impossible to effect. One embodiment of the present invention permits the physician to advance the second plunger into the second section, even when the distal end of the first plunger is not near and/or abutting the distal end of the first section. Once the second plunger passes through the cement in the first section, and enters the second section, cement will be displaced from the second section. Due to the decreased cross-sectional area of the second plunger and second section (as compared to the first plunger and first section), the second plunger is easier to push through the cement in the first section and cement can more easily be dispensed from the second section at higher pressures and/or lower volumes.

The disclosed filler instrument may be used to introduce filler material through a cannula into a cavity created within a bone, or may be used with vertebroplasty-type techniques to introduce filler material directly into the vertebral body without prior formation of a cavity. Where prior cavity-formation is not required and/or desired, and vertebroplasty-like techniques will be used, the filler instrument can incorporate a needle-point at the distal end of the instrument, or the diameter of the second section can be significantly reduced to allow passage of the instrument through the lumen of a spinal needle assembly. Alternatively, one or more of the sections of the filler instrument could comprise a commercially available spinal needle assembly (such as a Bone Marrow Biopsy Needle No. 508627, available from Becton Dickinson & Co., Franklin Lakes, N.J., 07417). If desired, one or more plunger assemblies of varying sizes and lengths could be provided to accommodate differing spinal needle assemblies.

If desired, the filler instrument can be pre-loaded with filler material, introduced through soft tissues and into the vertebral body, used to inject filler material, and removed, quickly and easily without need for tool exchanges during the operation. For example, where the end plates of the vertebral body have depressed to a point where an expandable structure cannot be safely inserted and/or expanded within the vertebral body, bone cement can be injected under pressure through a needle directly into the cancellous bone of the vertebral body (without cavity formation). The bone cement penetrates cancellous bone.

To reduce flow resistance to the filler material, the filler instrument can possess an increasing interior diameter, as shown in FIGS. 11A, 11B, or 11C. The reduced flow resistance would make possible the use of more viscous cement, to thereby further reduce the possibility that the cement would exude from the vertebral body.

FIGS. 17A through 17D and FIG. 18 depict an alternate embodiment of a filler instrument constructed in accordance with the teachings of the present invention. Because many of the features of this embodiment are similar to those previously described, like reference numerals will be used to describe similar components. In this embodiment, the first ram assembly 700A further comprises an increased cross-sectional tip opening 850 within the distal end 715A of the assembly 700A. This tip opening 850 corresponds to a increased cross-sectional plunger tip 855 on the second plunger 755. During use of the filler instrument 600A, while the first plunger 705A is advanced, the plunger tip 855 seats within the tip opening 850, desirably preventing the second plunger 750A from moving axially in response to the increased pressure of the filler material. If desired, a clip (not shown) can be utilized to secure the second plunger to the first plunger. Once the first plunger 705A has been advanced to its desired position, the clip (not shown) can be removed from the notch 765A, and the second plunger 750A advanced as previously described.

FIGS. 19A through 19D depict another alternate embodiment of a filler instrument 600B constructed in accordance with the teachings of the present invention. Because many of the features of this embodiment are similar to those previously described, like reference numerals will be used to describe similar components. In this embodiment, the first ram assembly 700B comprises a check valve 900 located at the distal tip 715 of the assembly 700B. The check valve 900 will desirably prevent filler material from travelling through the second ram opening 720B as the first plunger 705B is advanced. Once the first ram assembly 700B is advanced to its desired position, and the second plunger assembly is advanced through the second ram opening, the check valve 900 permits passage of the second plunger into the first and second sections as previously described.

The features of the invention are set forth in the following claims.

We claim:

1. A method comprising accessing cancellous bone through a percutaneous access path in soft tissue, forming a cavity in cancellous bone including providing a cavity forming tool, advancing the cavity forming tool through the percutaneous access path into cancellous bone, and manipulating the cavity forming tool to form the cavity, providing an instrument for introducing a filling material into the cavity comprising a first chamber section having a first volume and a second chamber section having a second volume less than the first volume, the first and second chamber sections being in series relation with the second chamber section being distal of the first chamber section, inserting at least a portion of the second chamber section through the percutaneous access path, and delivering a first volume of bone filling material into the cavity through the subcutaneous access path by advancing a first plunger through the first chamber section to express filling material from the first chamber section through the second chamber section into the cavity, the first plunger being too large to enter the second chamber section, delivering a second volume of bone filling material into the cavity through the subcutaneous access path by advancing a second plunger through the second chamber section to express filling material residing in the second chamber section into the cavity, the second volume being less than the first volume.

2. A method according to claim 1
wherein the cavity forming tool that is provided includes an expandable body.

3. A method according to claim 2
wherein the expandable body expands by inflation.

4. A method according to claim 2
wherein the expandable body comprises a balloon.

5. A method according to claim 1
wherein manipulating the cavity forming tool compresses cancellous bone.

6. A method according to claim 1
wherein manipulating the cavity forming tool moves fractured cortical bone.

7. A method according to claim 1
wherein the cavity forming tool that is provided includes an elongate member sized and configured to pass through the access path.

8. A method according to claim 7
wherein the elongate member comprises a catheter.

* * * * *